(12) United States Patent
Mody et al.

(10) Patent No.: US 8,657,815 B2
(45) Date of Patent: Feb. 25, 2014

(54) DELIVERY SYSTEM FOR DELIVERING A MEDICAL DEVICE TO A LOCATION WITHIN A PATIENT'S BODY

(75) Inventors: Dinesh I. Mody, Pleasanton, CA (US); Ketan Shroff, Pleasanton, CA (US); Dany Berube, Fremont, CA (US)

(73) Assignee: MicroCube, LLC, Fremont, CA (US)

( * ) Notice: Subject to any disclaimer, the term of this patent is extended or adjusted under 35 U.S.C. 154(b) by 1507 days.

(21) Appl. No.: 12/027,215

(22) Filed: Feb. 6, 2008

(65) Prior Publication Data
US 2008/0188850 A1    Aug. 7, 2008

Related U.S. Application Data

(60) Provisional application No. 60/899,905, filed on Feb. 6, 2007.

(51) Int. Cl.
*A61B 18/18* (2006.01)
(52) U.S. Cl.
USPC ............................................. 606/41; 606/45
(58) Field of Classification Search
USPC ............................................... 606/32–45
See application file for complete search history.

(56) References Cited

U.S. PATENT DOCUMENTS

| | | | |
|---|---|---|---|
| 5,263,493 A | 11/1993 | Avitall | |
| 5,387,219 A | 2/1995 | Rappe | |
| 5,487,385 A | 1/1996 | Avitall | |
| 5,637,090 A * | 6/1997 | McGee et al. | 600/374 |
| 5,687,723 A | 11/1997 | Avitall | |
| 5,738,683 A | 4/1998 | Osypka | |
| 5,800,482 A | 9/1998 | Pomeranz et al. | |
| 5,885,278 A | 3/1999 | Fleischman | |
| 5,895,417 A | 4/1999 | Pomeranz et al. | |
| 5,997,536 A | 12/1999 | Osswald et al. | |
| 6,032,077 A | 2/2000 | Pomeranz | |
| 6,152,920 A | 11/2000 | Thompson et al. | |
| 6,190,382 B1 | 2/2001 | Ormsby et al. | |
| 6,217,528 B1 | 4/2001 | Koblish et al. | |
| 6,241,754 B1 | 6/2001 | Swanson et al. | |
| 6,330,473 B1 | 12/2001 | Swanson et al. | |
| 6,430,426 B2 | 8/2002 | Avitall | |
| 6,468,272 B1 | 10/2002 | Koblish et al. | |
| 6,544,262 B2 | 4/2003 | Fleischman | |
| 6,607,505 B1 * | 8/2003 | Thompson et al. | 604/95.04 |
| 6,613,046 B1 | 9/2003 | Jenkins et al. | |
| 6,663,625 B1 | 12/2003 | Ormsby et al. | |
| 6,893,439 B2 | 5/2005 | Fleischman | |
| 6,908,464 B2 | 6/2005 | Jenkins et al. | |
| 6,916,306 B1 | 7/2005 | Jenkins et al. | |

(Continued)

*Primary Examiner* — Linda Dvorak
*Assistant Examiner* — Amanda Scott
(74) *Attorney, Agent, or Firm* — Levine Bagade Han LLP

(57) ABSTRACT

Devices, systems and methods are provided for deployment of one or more functional devices, such as therapeutic or diagnostic medical devices, or positioning devices, at various locations relative to a defined operative path. The devices, systems, and methods can include a guide system and a positioning element. The guide system defines the operative path when deployed within a patient's body. The positioning element cooperates with the guide system to define one or more positions relative the defined operative path from which the one or more functional devices are deployed. The present inventions allow for the accurate and reliable placement of the one or more functional devices at the one or more positions relative the operative path. In one embodiment, the functional device is an ablation device adapted to ablate cardiac tissue for the treatment of cardiac arrhythmias, such as atrial fibrillation.

12 Claims, 37 Drawing Sheets

(56) References Cited

U.S. PATENT DOCUMENTS

| | | |
|---|---|---|
| 7,011,655 B2 | 3/2006 | Thompson et al. |
| 7,029,471 B2 | 4/2006 | Thompson et al. |
| 7,052,492 B2 | 5/2006 | Swanson et al. |
| 7,115,122 B1 | 10/2006 | Swanson et al. |
| 7,175,619 B2 | 2/2007 | Koblish et al. |
| 7,182,764 B2 | 2/2007 | Jenkins et al. |
| 7,303,560 B2 | 12/2007 | Chin et al. |
| 2001/0007927 A1 | 7/2001 | Koblish et al. |
| 2001/0044625 A1 | 11/2001 | Hata et al. |
| 2002/0002329 A1 | 1/2002 | Avitall |
| 2002/0004631 A1 | 1/2002 | Jenkins et al. |
| 2002/0087151 A1 | 7/2002 | Mody et al. |
| 2002/0151889 A1 | 10/2002 | Swanson et al. |
| 2002/0161422 A1 | 10/2002 | Swanson et al. |
| 2003/0014049 A1 | 1/2003 | Koblish et al. |
| 2003/0050630 A1 | 3/2003 | Mody et al. |
| 2003/0153967 A1 | 8/2003 | Koblish et al. |
| 2003/0195406 A1 | 10/2003 | Jenkins et al. |
| 2004/0111020 A1 | 6/2004 | Long |
| 2004/0147911 A1 | 7/2004 | Sinofsky |
| 2004/0243107 A1 | 12/2004 | Macoviak et al. |
| 2005/0015083 A1 | 1/2005 | Koblish et al. |
| 2005/0049585 A1 | 3/2005 | Fleischman et al. |
| 2005/0059990 A1 | 3/2005 | Ayala et al. |
| 2005/0070887 A1 | 3/2005 | Taimisto et al. |
| 2005/0267461 A1 | 12/2005 | Cao et al. |
| 2006/0009759 A1 | 1/2006 | Chrisitian et al. |
| 2006/0142752 A1* | 6/2006 | Ormsby et al. ............... 606/33 |
| 2006/0217694 A1* | 9/2006 | Chin et al. ................... 606/15 |
| 2007/0213583 A1 | 9/2007 | Kim et al. |
| 2007/0219546 A1 | 9/2007 | Mody et al. |
| 2007/0270794 A1 | 11/2007 | Anderson et al. |
| 2007/0282256 A1 | 12/2007 | Hu et al. |

* cited by examiner

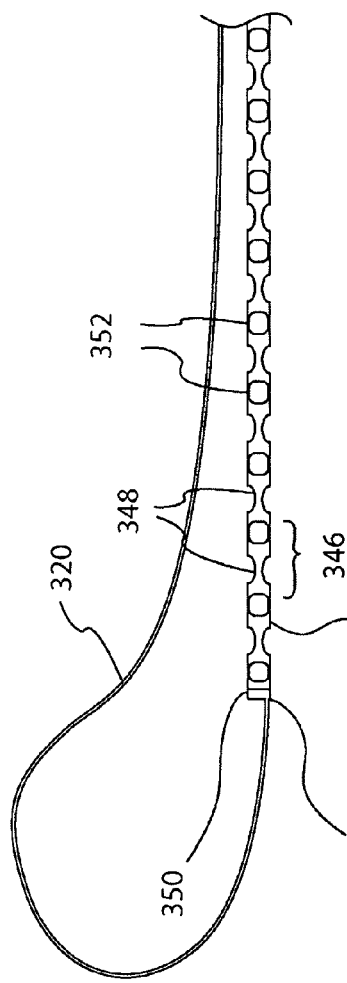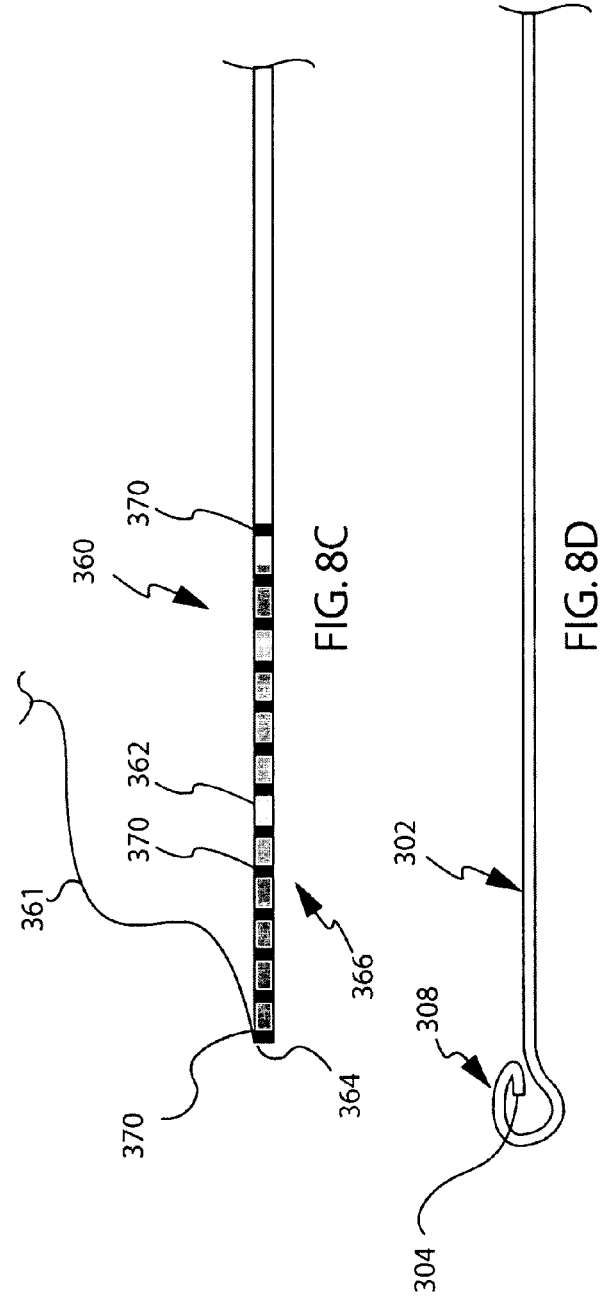
FIG. 8B
FIG. 8C
FIG. 8D

DELIVERY SYSTEM FOR DELIVERING A MEDICAL DEVICE TO A LOCATION WITHIN A PATIENT'S BODY

CROSS-REFERENCE TO RELATED APPLICATIONS

This application is a non-provisional of U.S. Provisional Application No. 60/899.905 filed Feb. 6, 2007 which is incorporated herein by reference in its entirety.

FIELD OF THE INVENTION

This invention relates to delivery systems suitable for positioning various medical devices within a patient's body and, more specifically, to delivery systems designed to cooperate with certain therapeutic and diagnostic devices, or further positioning device, for positioning such devices within a patient's heart for the treatment of cardiac arrhythmias, such as atrial fibrillation.

BACKGROUND OF THE INVENTION

Very often there is a need to position a medical device, be it a diagnostic device, therapeutic device, or a positioning device to name a few, within the body of a patient as part of performing a medical procedure. Due to the nature of the living body which moves with respiration and other bodily functions, such positioning can be daunting, especially where the medical device must be positioned within a confined space.

One example where such a need exists is in the treatment of cardiac arrhythmias, and more specifically atrial fibrillation (AF). AF is a disorder found in more than 2 million Americans. A heart in normal sinus rhythm receives an electrical signal from which it develops the well coordinated heart beat. AF occurs when something imparts a change to the received electrical signal resulting in uncontrolled and uncoordinated beating of the atria, the atria receiving multiple signals which command the atrial chambers to beat in an uncoordinated manner.

While typically not fatal, the uncoordinated heart beat associated with AF results in blood pooling and clotting which, in turn, can lead to stroke. Approximately 15 percent of strokes occur in people with AF.

Ablation catheter systems are commonly used in the left atrium to treat atrial fibrillation. The ablation catheter systems may incorporate an ablating portion which is strategically placed upon the soil tissue of the left atrium. One or more lesions are then created as part of a desired lesion set or pattern in order to treat AF.

Catheter ablation of the left atrial tissue to create a desired lesion set can be problematic due to positioning constraints put on the user, primarily an electrophysiologist. The user must remotely and percutaneously manipulate the ablating device to a desired point within the left atrium from which the ablating element can be energized creating a lesion, as part of a desired lesion set. Typically, catheter systems having distal end electrodes are guided to one of many positions and then activated to create such lesions. Such catheter systems, however, are highly problematic requiring a stable platform from which the ablating device can be accurately positioned at a desired location. Known systems require tremendous amounts of time to create desired lesion sets clue to positioning problems and the configuration of the ablating device itself one which is directed to the creation of point ablations rather than linear lesions. Some desired lesions may require a user to create numerous such point ablations.

What is needed is a delivery system which can quickly and easily deploy an ablation device, as well as other functional devices, to create a desired lesion pattern through the accurate positioning and ablation of various target tissue sites, the ablations which together form the desired lesion pattern.

SUMMARY OF THE INVENTION

Accordingly, a delivery system for delivering a functional device to a location within a patient's body is provided. In one embodiment the system includes a deployable guide system and positioning element. The guide system includes a longitudinal axis having a predetermined shape and defining an operative path when the guide system is deployed within the body. The guide system is deployable and defines the path without the need to contact biological tissue. The positioning element is adapted to operably cooperate with the deployable guide system to define a position relative to the defined path from which the functional device is deployed, for example the functional device may be slidably coupled to the positioning element allowing for such deployment. Furthermore, the functional device is deployed at the position relative the defined path without further assistance, physical contact for example, from the guide system.

In another embodiment, the delivery system comprises an elongate introducer, a deployable elongate guide member and a positioning clement slidably and rotatably coupled to the guide member, the elongate guide member and positioning element slidably and rotatably positioned within the elongate introducer. The deployable elongate guide member has a longitudinal axis which defines a desired closed-loop operative path when deployed past the distal opening of the elongate introducer and within a patient's body. The positioning element is at least slidably coupled to the elongate guide member to define a position relative to the defined path from which a functional device is deployed.

In yet another embodiment, a delivery system is provided for delivering a functional device to a location within a patient's body, the delivery system comprising an elongate introducer, a deployable elongate guide member and a positioning element fixedly attached to, or otherwise integral to, the elongate guide member. The deployable elongate guide member defines an operative path when deployed past the elongate introducer and within a patient's body. The positioning element cooperates with the elongate guide member to define a position relative to the defined path from which a functional device is deployed.

In one aspect of the invention the functional device is deployable from the position along the defined operative path without requiring further engagement with the deployable guide system at a point along the elongate guide member distal to such position.

In another aspect of the invention the elongate guide member, as part of a guide system, includes a distal end which is positioned within the body when the elongate guide member is deployed. The single-ended elongate guide member may be linear, curvilinear or preshaped to address a specific desired operative path along the posterior wall of the heart between the left and right inferior pulmonary veins for example. In one aspect of the invention a positioning element slidably coupled to a preshaped single-ended elongate guide member deployed within a hollow organ cooperates with the deployed guide member to access a majority of the tissue surface of the hollow organ without redeployment of the guide member.

In yet another aspect of the invention the elongate guide member, as part of a guide system, is adapted to define or form a loop-shape when deployed. The elongate member may have a rectangular cross-sectional geometry to encourage deflection in a single plane. In contrast, the elongate member may have a circular cross-sectional geometry allowing the loop-shaped guide member to be directionally positioned, or otherwise steerable, further allowing a user greater flexibility in defining the operative path.

BRIEF DESCRIPTION OF THE DRAWINGS

The assembly of the present invention has other objects and features of advantage which will be more readily apparent from the following description of the various modes of carrying out the invention, when taken in conjunction with the accompanying drawings, in which:

FIGS. 8A-8D are a series of elevation views depicting yet another embodiment of a delivery system in accordance with the present invention.

DETAILED DESCRIPTION OF THE INVENTION

General Embodiment

Figure 1:
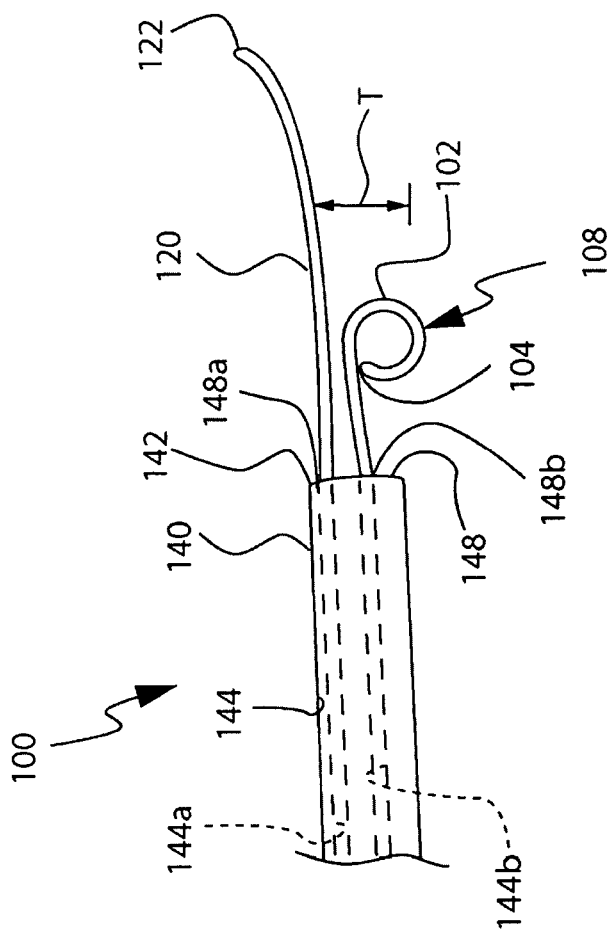
FIG. 1 is a side elevation view of a first embodiment of a delivery system in accordance with the present invention.

Generally, the present invention provides a stable platform from which a functional device can be easily and accurately deployed toward a desired target tissue location or area within a patient's body for the purpose of safely and effectively performing one or more medical procedures. In its simplest form, the delivery system comprises a guide system and a positioning element. The guide system is adapted to define a desired operative path when deployed within a patient's body, and the positioning element is adapted to operably cooperate with the guide system, for example translatable along at least a portion of the guide system, to define a position along the operative path from which the functional device is deployed. The positioning element is further adapted to provide an initial direction toward which the functional device is deployed.

As discussed in greater detail below, the stability of the guide system can come from the design of the guide system itself or through contact with surrounding tissue. While tissue contact is not required for deployment of the guide system within the body, in some instances it may be advantageous to deploy the guide system until such contact with surrounding tissue is achieved, for example when it is desirable to deploy the functional device with respect to a known anatomical reference, the anatomical reference providing a stable base for the deployed guide system from which the functional device is deployed, or when the guide system is deployed adjacent a target tissue area providing a stable platform from which the functional device can be deployed to reach the target tissue area. In certain embodiments discussed below, the positioning element may include certain preshaped portions to further enable such access to the desired target tissue areas. In other embodiments, the delivery system may include one or more delivery sheaths which cooperate with the guide system and positioning element to provide further positioning options to the user.

The guide system, when deployed within a patient's body, in addition to providing a stable point from which a functional device is deployed, is adapted to cooperate with the positioning element, as discussed in greater detail below, to provide greater accuracy and flexibility in positioning functional devices at desired locations within a patient's body relative to a desired operative path. Cooperating with the positioning element, the guide system is adapted to allow a user to easily return back to a known position along the operative path, if desired, to repeat the performance of the medical procedure, or a portion thereof, or perform an additional procedure with respect to that position. Moreover, the guide system is adapted to allow for the performance of multiple medical procedures at a known location relative to the position along the operative path via deployment of multiple functional devices either simultaneously, or individually through sequential deployment of each functional device corresponding to a given medical procedure. For illustration purposes only, in the treatment of AF, mapping of various electrophysiological signals within the left atrium of a patient's heart can be performed before, during, or after ablation of a target tissue as part of a desired lesion pattern, the one or more functional device deployed as required. Such mapping and ablation activities can involve multiple functional devices performing the desired medical procedure at various positions relative to the path.

Furthermore, the guide system can be adapted for the performance of a specific medical procedures such adaptation resulting in the creation of a desired operative path related to the performance of the specific medical procedure.

Additionally, in some embodiments, the positioning element is adapted to provide a known reference with respect to the guide system, and hence the desired operative path such that a series of related medical procedures can be performed at desired locations relative to the operative path. For example, the functional device may be an ablation device for producing a series of continuous lesions as part of a desired lesion pattern within the left atrium of a patient's heart in the treatment of AF, the positioning element designed to further position the ablating portion of the ablation device at a position relative the operative path. In this way, the guide system can be deployed, and in cooperation with the positioning element, positions the ablation device at various locations relative the operative path such that the continuous series of lesions are created. As will be more readily understood with reference to further discussion below, such a procedure can be performed through simple and controlled user inputs. The guide system or positioning element can include additional elements to further aid in developing a know relationship between the functional device and the path. For example, the guide system and positioning element can incorporate various elements which are radiopaque and fluoresce with use of a fluoroscopy system. The elements can be shaped to provide orientation information to better depict the various components of the delivery system. Such elements can perform other functions, therapeutic, diagnostic, positioning, or otherwise, as well.

While not necessary, in some preferred embodiments the positioning element has a flexibility less than that of the portion of the guide system with which the positioning element cooperates such that substantial deformation of the guide system, and hence the associated operative path, does not occur during such cooperation. Furthermore, due to space constraints, in other embodiments the positioning element may be first deployed, followed by deployment of the guide system and definition of the operative path.

In general operation, the guide system is deployed within a patient's body to define the desired operative path. Once the guide system is deployed, the positioning element is operated and cooperates with the guide system to define the position along the path from which the function device is deployed. For illustration purposes only, the positioning element may be a sheath adapted to be slidably coupled to the guide system, the sheath being advanced over a portion of the guide system, a distal opening of the sheath defining the position along the path from which the functional device is deployed, as well as defining the direction toward which the functional device is deployed. In the case of a positioning element in the form of a sheath, the sheath may have a flexibility less than that of the guide system such that advancement of the sheath along the guide system does not act to substantially deform the guide system and the path it defines. Moreover, the sheath may include an additional steering mechanism to allow for greater flexibility in accessing various sites within a patient's body, within a hollow organ such as the heart for example. In such embodiments, redeployment of the guide system can be reduced or eliminated, providing for a correspondingly decrease in procedural time.

Once the guide system and positioning element are deployed within the patient, the functional device can then be deployed and the medical procedure, or a portion thereof, can be performed. For the discussion herein a functional device may be any device used for the performance of a medical procedure, or a portion thereof, including, but not limited to, therapeutic devices such as ablation devices for imparting a treatment relative a target tissue, diagnostic devices such as mapping catheters for providing physiological information regarding a target tissue or positioning devices which include elements for providing additional positioning of additional functional devices. The functional device need not have a specific physical structure, for example the delivery system can be adapted to deploy a chemical ablating agent at a desired location or deploy an additional fluid used during, and in support of, the medical procedure, for example deployment of contrast agent to provide a clearer view of the anatomy in support of a procedure performed within a patient's heart.

In light of the functional devices listed immediately above, it should be understood, however, that certain devices have specific features which are particularly advantageous when combined with the various embodiments disclosed herein. For example, ablation devices, including ablating portions having one or more ablating elements mounted thereon, which are adapted to be formed into shapes defining an offset between the ablation device and the guide system, allow for application of a torsional force with respect to the guide system, encouraging tissue contact therewith. It is important to note that the offset nature between the functional device and the guide system, and hence the defined operative path, has other advantages as well. For example, many current ablation devices which include loop shaped ablating portions require such loop-shaped devices to be positioned at multiple locations along the desired ablation line. This, in turn, requires redeployment of the ablation device to create each lesion as part of a desired lesion pattern. In contrast, the present invention advantageously provides a stable platform from which an ablation device can be deployed accurately and reliably from multiple positions relative to an operative path such that numerous lesions as part of a desired lesion pattern, or the complete lesion pattern itself, can be created, with minimal to no redeployment of the guide system required, saving procedural time and ultimately cost.

Since the present invention provides stable and accurate placement of functional devices at known locations relative to an operative path, the present invention reduces the dependency on costly imaging systems which attempt to render the operative setting in a partially simulated three-dimensional space, and costly deployment systems requiring huge capital and specific compatibility with the device used during the procedure, such as certain magnetic navigation systems requiring the positioning of large magnets adjacent the patient for device control. Failure of such systems may lead to corresponding failures with respect to the desired medical procedure to be performed.

Delivery System: Single-Ended Guide Member

Turning to FIG. 1, a side elevation view of a first embodiment of a delivery system in accordance with the present invention is depicted. As shown in its simplest form, delivery system 100 is adapted to provide a stable platform from which a functional device, such as functional device 102, is deployed. Generally, delivery system 100 comprises a guide system or rail 120 having a distal end 122 and a positioning element or sheath 140 having a distal end 142. Distal end 122 may comprise a blunt, or flexible, or otherwise Atraumatic, tip. Rail 120, as with similar such elements disclosed herein, may be manufactured from any suitable biocompatible materials including, but not limited to, various biocompatible polymers or metals such as Nitinol, stainless steel or titanium. Rail 120 may include one or more navigational markers to enable a user to better visualize open-ended rail 120 within a patient's body. For illustration purposes only, radiopaque markers may be used.

Positioning sheath 140 is formed of any suitable biocompatible material, such as PTFE, expanded PTFE or the like. Sheath 140 is adapted to include at least one lumen 144 therethrough defining a distal opening 148 and adapted to slidably and rotatably receive the rail 140 and functional device 102 therein. One important feature of the present invention is the ability to encourage contact between a functional device and a target tissue surface. This is accomplished by offsetting the functional device from the guide system such that application of a torsional force to the functional device with respect to the guide system results in increased contact force between at least a portion of the functional device and a target tissue surface.

An offset between the functional device 102 and the rail 120 can be achieved in at least one of two ways. First, the functional device 102 can include a working end 108 defining a shape such that an offset exists between at least a portion of the working end 108 of the functional device 102 and the guide system 120, such offset depicted as distance T. Alternatively, sheath 140 can include individual lumens 144a, 144b for slidably and rotatably receiving the guide system 120 and functional device 102 therein, respectively. Each lumen 144a, 144b can define a corresponding distal sheath opening 148a, 148b adapted to be positioned at end 142 such that a distance therebetween is defined, providing the desired offset, both the guide system or rail 120 and the functional device 102 being slidably and rotatably received within the corresponding lumen 148a, 148b, respectively. It should be noted that the sheath 140 can include additional lumens for deployment of additional functional devices, as described herein. Such additional lumens may be further used for deployment or retraction of bodily fluids, as part of a medical procedure.

Lumens 144, including 144a and 144b, preferably include lubricious inner surfaces, or otherwise are adapted to cooperate with the guide rail 120 and functional device 102, to facilitate smooth operation of both the guide rail 120 and functional device 102 translatable and rotatable therein. As discussed above, the lumens 144a, 144b can be displaced at the distal end of sheath 140 allowing the positioning of a distal portion of the functional device 102 offset from a longitudinal axis of the guide rail 120. In this way, the functional device 102 can be rotated with respect to the guide rail 120 providing a torsional force to the distal portion 108 of the functional device 102 with respect to the rail 120 encouraging tissue contact therewith.

In general operation, the guide sheath 140 is deployed within a patient's body. Once deployed, the guide system or rail 120 is advanced from the sheath 140, the distal end 122 of the rail 120 exiting the distal opening 144 of lumen 142.

In a preferred embodiment, open-ended rail 120 is a stiff stylet made of Nitinol. In a preferred embodiment, guide sheath 140 is made of ePTFE. The combination of open-ended rail 120 and guide sheath 140 are used to define the location and the initial trajectory of introduction of functional device 108. In one method embodiment, the user introduces, or otherwise deploys, open-ended rail 120 into a patient's body. Open-ended rail 120 is positioned such that at least a portion of open-ended rail 120 is in the vicinity of a target tissue or anatomical region. Thereafter, the user moves or advances guide sheath 140 over the open-ended rail 120, the distal end 142 of guide sheath 140 defining a position relative to the operative path and further defines an initial direction toward which the functional device 108 is deployed, toward a target tissue for example.

Open-ended rail 120 may be stabilized in the anatomy, if desired, by a variety of methods. For example, one or more portions of the open-ended rail 120 may be positioned within an anatomical cavity. Alternatively, rail 120 of delivery system 100 can include one or more anchoring devices adapted to secure one or more portions of the delivery system 100 to biological tissue. Once the distal end of rail 120 is anchored, that portion of rail 120 deployed within the body, for example within the heart, defines an operative path over which the positioning element, such as sheath 140, travels.

Figure 2A:
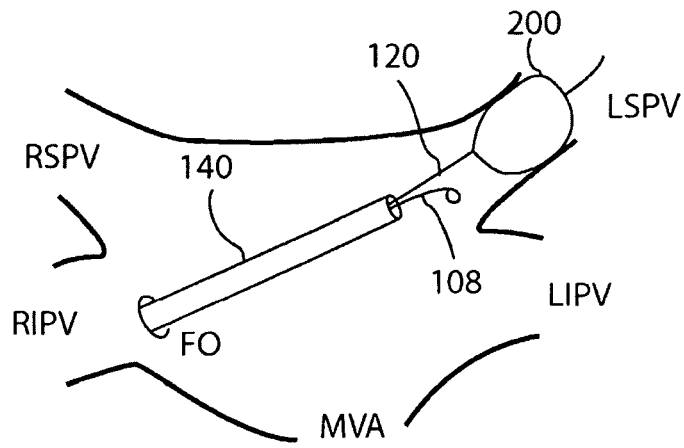
FIGS. 2A-2C are perspective views of alternative embodiments of the delivery system of FIG. 1 including exemplary anchoring elements.
Figure 2B:
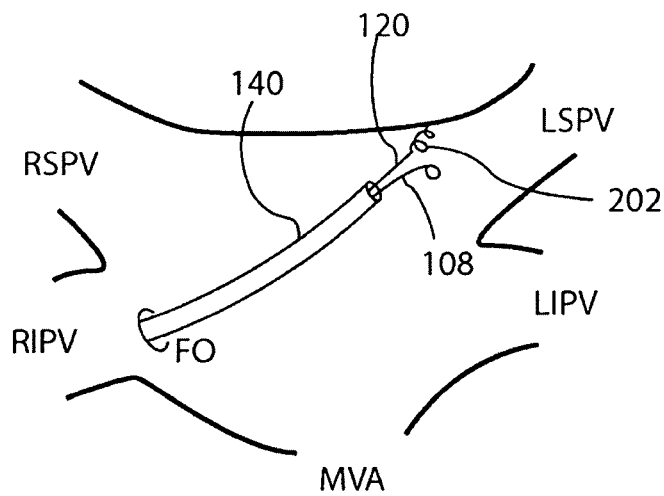
Figure 2C:
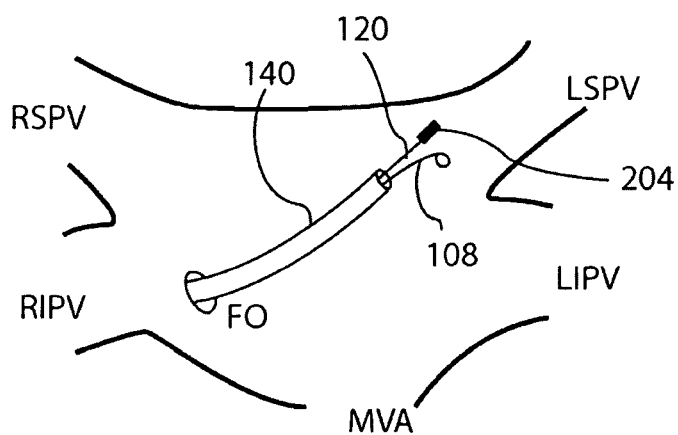

With reference to FIGS. 2A through 2C a number of exemplary anchoring devices are depicted in use within a left atrium of a patient's heart, the left atrium including left and right, superior and inferior, pulmonary veins LSPV, LIPV, RSPV, RIPV, respectively, and the mitral valve annulus MVA. In FIG. 2A, as depicted, the distal region of open-ended rail 120 comprises an anchoring balloon 200. Anchoring balloon 200 may be a compliant balloon, a non-compliant balloon or a semi-compliant balloon. In the method embodiment shown in FIG. 2A, anchoring balloon 200 is anchored within the LSPV.

In FIG. 2B the distal region of open-ended rail 120 comprises an anchoring tip 202. For illustration purposes, anchoring tip 202 may be formed as a straight sharpened tip, a spiral loop portion having a sharp distal end, or a screw tip, or the like for anchoring the distal end of rail 120s. In the method embodiment shown in FIG. 2B, anchoring tip 202 is anchored on a superior surface of the left atrium.

In FIG. 2C the distal region of open-ended rail 120 comprises an anchoring magnet 204. Anchoring magnet 204 may be a permanent magnet or an electromagnet. Anchoring magnet 204 is subjected to an artificial magnetic field, such as on the epicardial surface opposing the position of magnet 204, which causes anchoring magnet 204 to press against a region on the wall of the left atrium. This in turns anchors open-ended rail 120 to the anatomy. In the method embodiment shown in FIG. 2C, anchoring magnet 204 is anchored on a superior surface of the left atrium. Other locations within the heart are also well suited, such as from within a pulmonary vein, on the posterior wall or anterior wall.

Figure 3A:
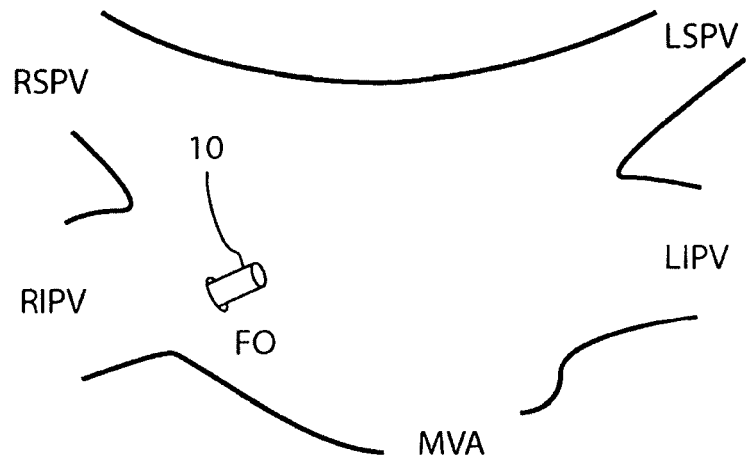
FIG. 3A-3G are a series of perspective views, in partial cross-section, of the heart illustrating an alternative embodiment of the delivery system of FIG. 1 having a guide system incorporating a curvilinear guide member.
Figure 3B:
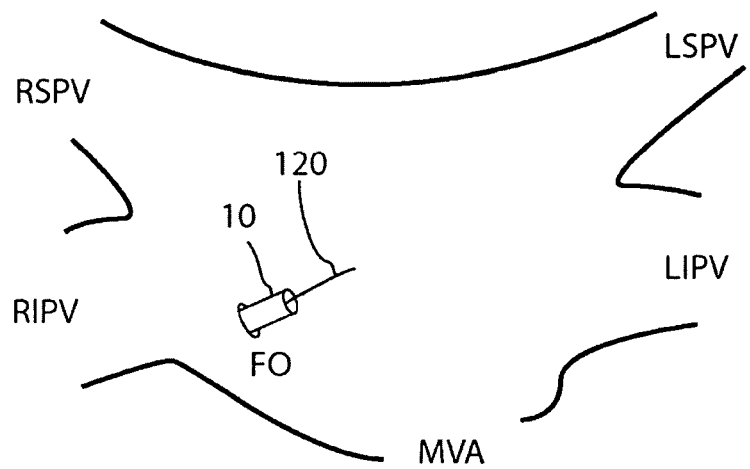

FIGS. 3A through 3G show the steps of a method of delivering a functional device, such as device 108, to a desired target tissue location using the delivery system 100 of FIG. 1. In FIGS. 3A through 3G, the left atrium is used as an exemplary target tissue location. As with other embodiments disclosed herein, delivery system 100 and methods associated thereto, can also be used to deliver functional devices to other anatomical regions including, but not limited to other regions of the heart, regions of the vasculature, regions of the GI tract, regions of the airway, regions within additional hollow organs or other bodily spaces beneath the skin. In FIG. 3A, an access path is created to the target tissue or anatomical region. In the embodiment shown, the access path is a trans-septal path from the right atrium into the left atrium via the lumen of a trans-septal sheath or introducer 10. In FIG. 3B, open-ended rail 120 is introduced into the anatomical region. In the embodiment shown, open-ended rail 120 is introduced into the left atrium through the lumen of trans-septal sheath 10.

Figure 3C:
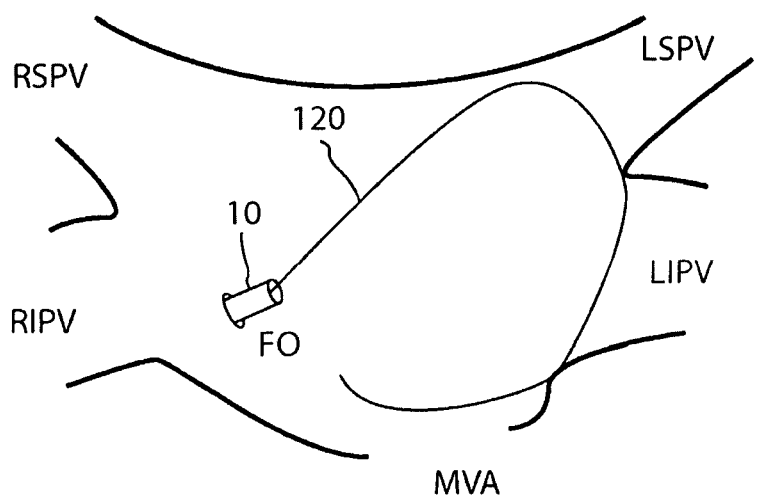
Figure 3D:
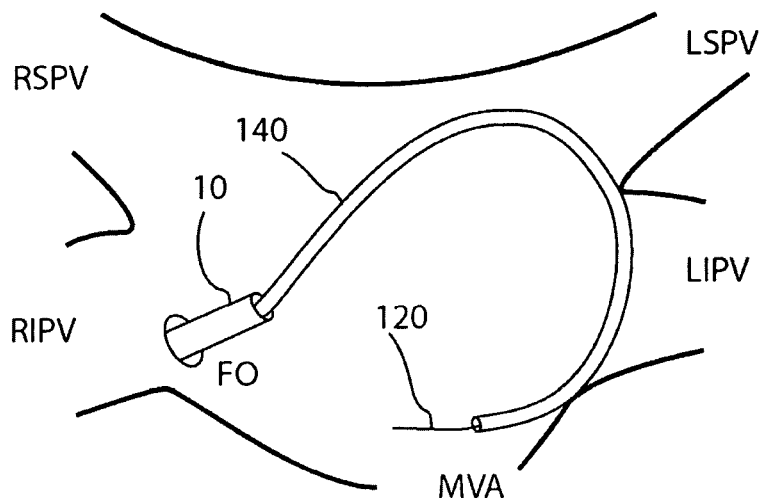

The lumen of trans-septal sheath 10 is preferable lined with a lubricious coating e.g. a PTFE coating or the like. As depicted in FIG. 3C, open-ended rail 120 is further advanced into the left atrium.

Figure 3E:
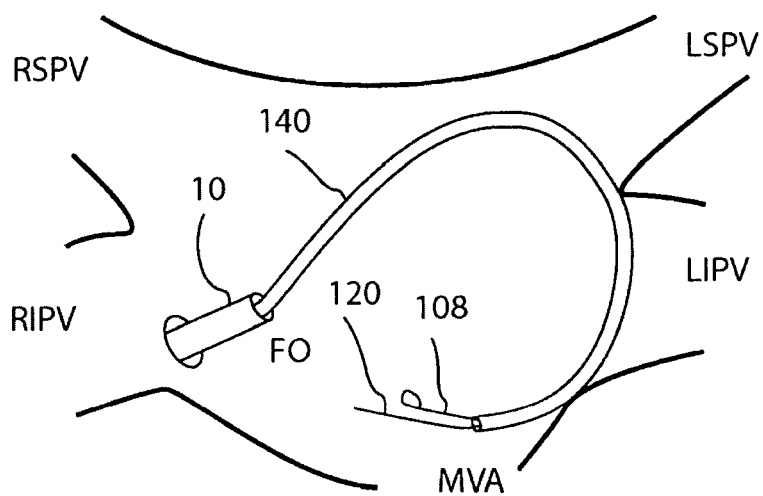
Figure 3F:
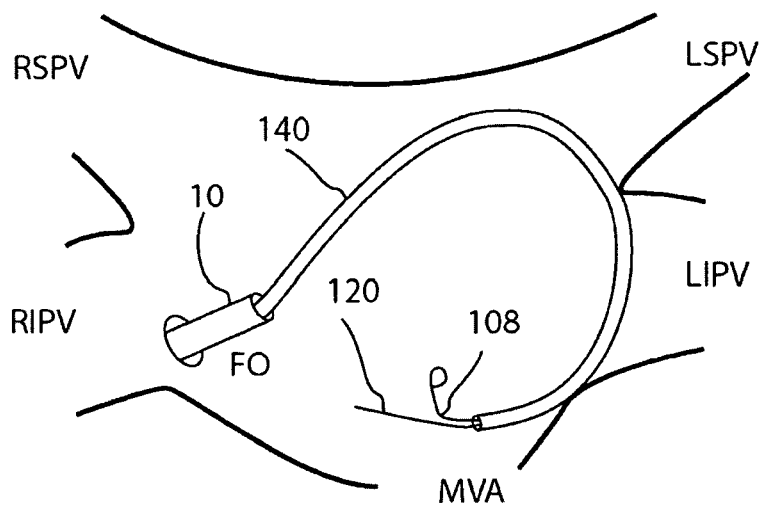
Figure 3G:
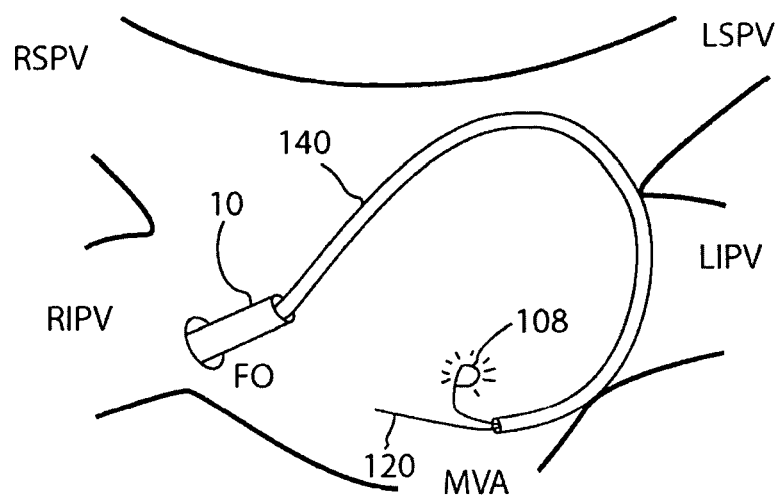

In the embodiment shown in FIGS. 3A through 3G, open-ended sheath 120 is preshaped. Thus, as open-ended rail 120 is introduced into the left atrium, it assumes its preshaped form. Open-ended rail 120 is positioned such that a portion of open-ended rail 120 is within the left pulmonary vein groove, as generally depicted in FIG. 3C. Once positioned within the left atrium, the preshaped rail 320 acts to define an operative path along which sheath 140 is advanced. More specifically, in FIG. 3D, guide sheath 140 is advanced over open-ended rail 120 until the distal end 142 of sheath 140 is positioned at a desired location. In this way, the distal end 142 defines the position along the rail 320 from which the functional device, such as functional device 108, is deployed. Thereafter, as depicted in FIG. 3E, functional device 108 is advanced through guide sheath 140 such that the distal end of functional device 108 emerges out of the distal end of guide sheath 140. Thereafter, in FIG. 3F, functional device 108 is steered to the target region in the anatomy. Functional device 108 may be steered to the target region by a variety of methods including, but not limited to advancing or withdrawing, torquing, or deflecting the distal end of the device. In the embodiment shown, functional device 108 comprises a deflectable or preshaped distal tip. Thereafter, in FIG. 3G, functional device 108 is used to perform a procedure in the left atrium, for example an ablation procedure for the treatment of AF.

Figure 4A:
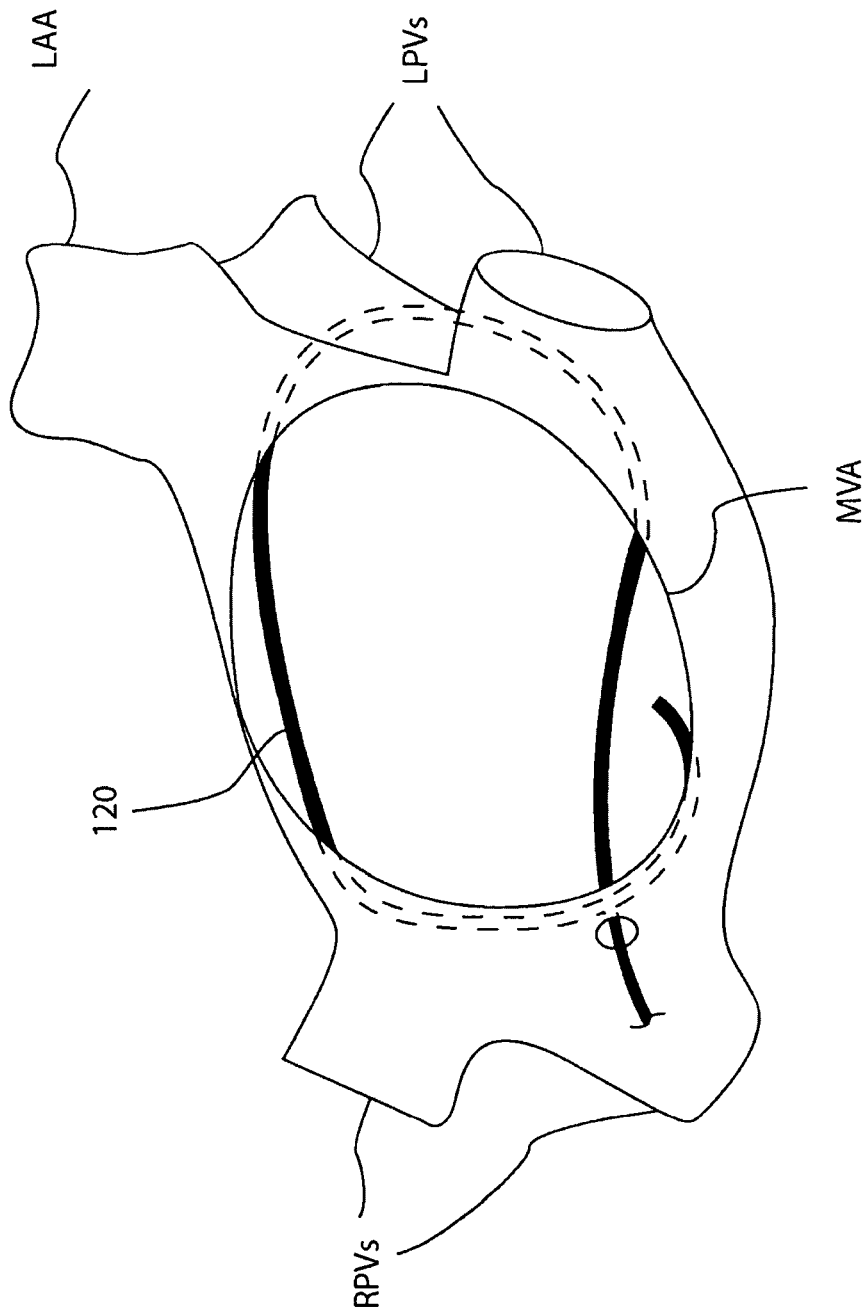
FIG. 4A-4G are a series of perspective views, in partial cross-section, of the heart illustrating an alternative embodiment of the delivery system of FIG. 1 having a guide system incorporating a curvilinear guide member, the guide member adapted to engage a surface of the heart.

Various embodiments of open-ended rail 120 can be designed for specific applications. For example, FIG. 4A shows a view of the left atrium of the heart through the mitral valve annulus depicting a deployed open-ended sheath that is designed to access the right pulmonary veins, left pulmonary veins and the superior roof of the left atrium. In FIG. 4A, open-ended rail 120 is preshaped. Open-ended rail 120 can be used to perform cardiac ablation procedures. Examples of such ablation procedures are ablation procedures to treat AF wherein one or more of the right pulmonary vein ostia surrounding lesions, left pulmonary vein ostia surrounding lesions and roofline lesions are created.

Figure 4B:
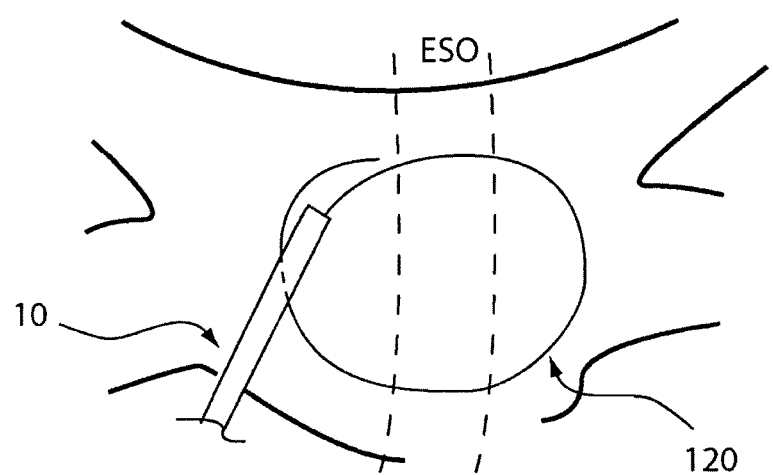
Figure 4C:
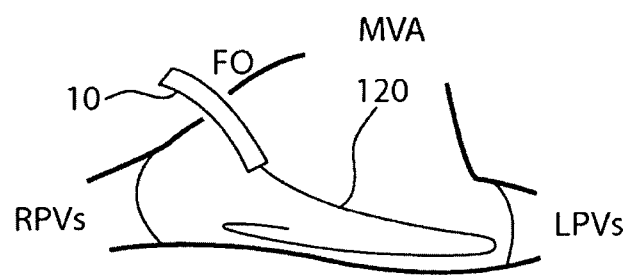

FIGS. 4B and 4C show two views of the left atrium depicting the placement of an embodiment of an open-ended rail designed to be stabilized on the posterior wall of the left atrium. In FIGS. 4B and 4C, open-ended rail 120 is preshaped. Open-ended rail 120 of FIG. 4 comprises a substantially circular preshaped distal section. The substantially circular distal section or region is at an angle with respect to the immediately proximal region of the open-ended rail 120. The angle is designed such that when open-ended rail 120 is introduced through a suitable trans-septal sheath, such as sheath 10, the substantially circular distal region presses against the posterior wall of the left atrium. Such a stabilized open-ended rail 120 can then be used to deliver functional devices to target locations on or around the posterior wall of the left atrium, or adjacent the pulmonary veins.

Figure 4D:
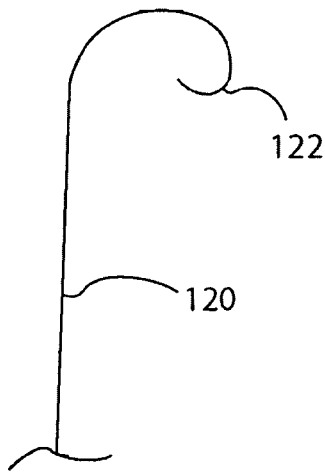

FIG. 4D shows a side view of the distal region of an embodiment of an open-ended rail comprising a curved distal tip. In FIG. 4D, distal end 122 of open-ended rail 120 is curved with a radius of curvature greater than the radius of a pulmonary vein ostia, preventing the curved distal tip 122 of rail 120 from entering the pulmonary vein ostia when inserted into the left atrium of the heart.

Figure 4E:
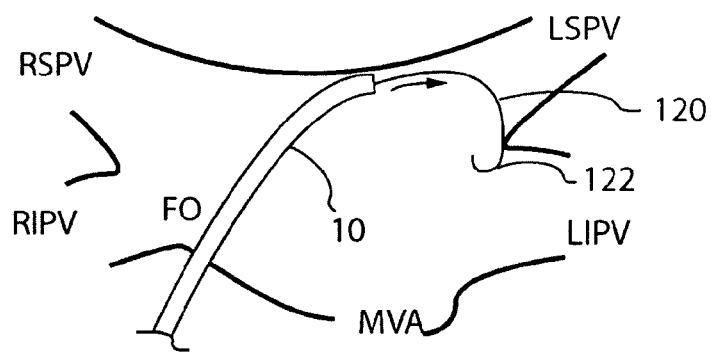
Figure 4F:
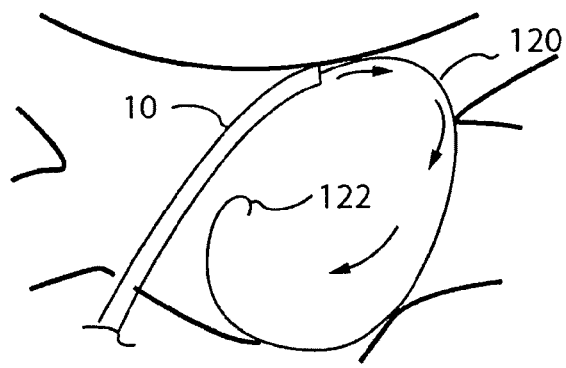
Figure 4G:
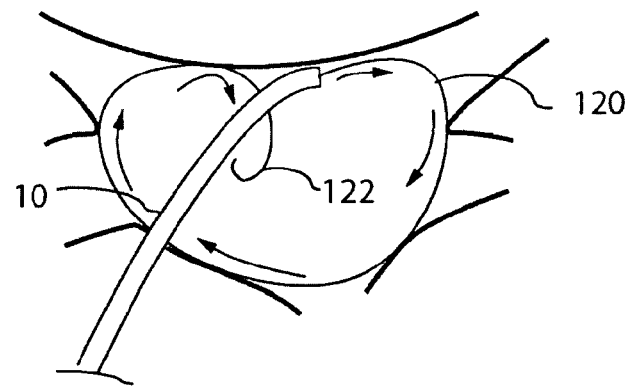

FIGS. 4E through 4G shows a view of the left atrium of the heart showing the steps of a method of using the open-ended rail of FIG. 4D to create an access path to multiple regions of the left atrium. In FIG. 4E, open-ended rail 120 is introduced into the left atrium through the lumen of a trans-septal sheath 300. Open-ended rail 120 is advanced such that distal tip 122 of open-ended rail 120 comes into contact with a region of the wall of the left atrium. Curved distal end 122 of open-ended rail 120 prevents open-ended rail 120 from entering a pulmonary vein. Therefore, open-ended rail 120 generally curls inside the left atrium as shown. In FIG. 4F, open-ended rail 120 is further advanced such that open-ended rail 120 curls further inside the left atrium. FIG. 4G shows the final position of open-ended rail 120 inside the left atrium. Open-ended rail 120 has curled inside the left atrium bounded by the ostia of the pulmonary veins, the mitral valve annulus and remaining portions of the wall of the left atrium. Thereafter, open-ended rail 120 can be used to deliver various functional devices to target regions on the walls of the left atrium. Examples of such regions include, but are not limited to the ostia of pulmonary veins, pulmonary veins, mitral valve annulus, posterior wall of the left atrium, to name a few.

Delivery System: Closed-Loop Rail

Figure 5A:
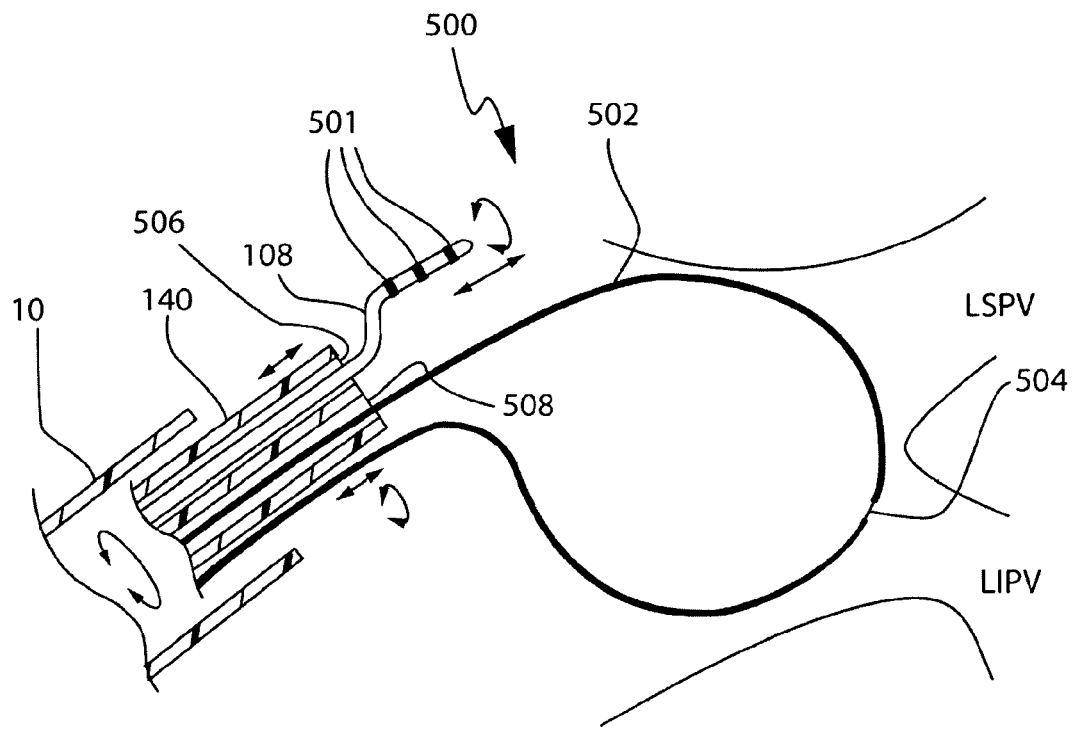
FIGS. 5A-5C are a series of views depicting another embodiment of a delivery system in accordance with the present invention.

FIG. 5A shows a sectional view through another embodiment of a delivery system 500 comprising a looped rail being used to deliver a functional device to the led atrium, in the embodiment shown, the delivery system 500 is being used to deliver a functional device 108 comprising one or more electrodes 501. In one embodiment, electrodes 501 are electrophysiological mapping electrodes. In an alternate embodiment, electrodes 501 are electrophysiological pacing electrodes. In an alternate embodiment, electrodes 501 are electrophysiological ablation electrodes. The distal-most region of functional device 108 is offset to a proximal region of functional device 108 as shown. This allows the user to access regions of the anatomy adjacent to the path defined by a looped rail 502. Such an offset also encourages contact between the functional device 108 and a target tissue through torsion of the functional device 108. Functional device 108 can also be rotated around its axis to enable the distal-most region of functional device 108 to access multiple anatomical regions without translating functional device 108. Functional device 108 can also be advanced or withdrawn. Functional device 108 is introduced into the anatomy through guide sheath 140 as shown in FIG. 5A. In the embodiment shown in FIG. 5A, guide sheath 140 has two lumens: a first lumen 506 for introducing functional device 108 and a second lumen 508 that encloses a part of looped rail 502. Guide sheath 140 is advanced into the anatomy, or withdrawn from the anatomy, over looped rail 502 and through trans-septal sheath 10. Guide sheath 140 can also be torqued within trans-septal sheath 10. In the embodiment shown in FIG. 5A, a looped rail 502 enters the anatomy through second lumen 508 of guide sheath 140 and leaves the anatomy through the region between guide sheath 140 and trans-septal sheath 10.

Looped rail 502 forms a loop in the anatomy when deployed and defines an operative path over which guide sheath 140 travels, the distal end of sheath 140 defining a position from which a functional device 108 is deployed. One or more ends of looped rail 502 can be advanced or withdrawn to define the shape of looped rail 502 in the anatomy. One or more ends of looped rail 502 can also be torqued to define the shape of looped rail 502 in the anatomy, in one embodiment, looped rail 502 comprises one or more preshaped loop portions. In the preferred embodiment shown in FIG. 5A, looped rail 502 comprises a stringy flexible joint 504. Stringy flexible joint 504 allows the user to introduce a sharp bend in the region of looped rail 502 containing stringy flexible joint 504. This in turn allows looped rail 502 to be introduced into the anatomy through a small lumen. Thereafter, the region of looped rail 502 containing stringy flexible joint 504 is removed from the anatomy by advancing one end of looped rail into the anatomy while withdrawing the other end of looped rail 504 from the anatomy.

In a method embodiment, looped rail 502 is introduced in the anatomy such that a desired loop is created. Thereafter, guide sheath 140 is advanced over looped rail 502 to a desired position. Thereafter, functional device 108 is introduced through guide sheath 140 such that the distal end of functional device 108 is located at a desired location relative the operative path defined by the deployed looped rail 502. Thereafter, functional device 108 is used to perform a procedure in the anatomy. The distal end of functional device 108 is navigated to the target region in the anatomy by one or more operational inputs including, for illustrative purposes only, advancing, withdrawing, or torquing one or both ends of looped rail 502, advancing, withdrawing, or torquing functional device 108, and/or advancing, withdrawing, or torquing guide sheath 140.

Figure 5B:
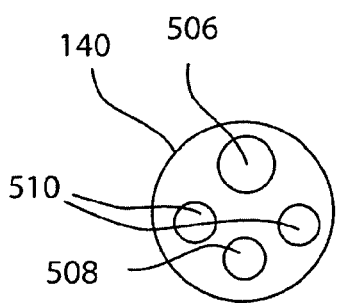
Figure 5C:
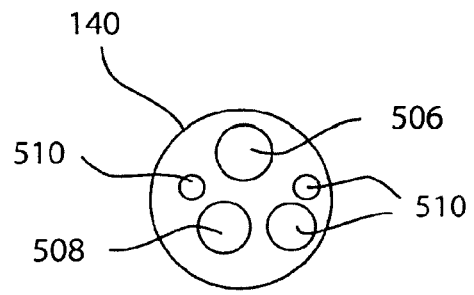

FIGS. 5B and 5C show cross sections of two alternate embodiments of the guide sheath of FIG. 5A. In FIG. 5B, guide sheath 140 comprises first lumen 506 for introducing functional device 108 and second lumen 508 that encloses a part of looped rail 502. Guide sheath 140 also comprises two additional lumens 510 for introducing or withdrawing one or more devices of fluids. In FIG. 5C, guide sheath 140 comprises first lumen 506 for introducing functional device 108 and second lumen 508 that encloses a part of looped rail 502. Guide sheath 140 also comprises three additional lumens 510 for introducing or withdrawing one or more devices (e.g. electrophysiological mapping devices) or fluids. One or more of additional lumens 510 may have a non-circular cross section e.g. a crescent shaped cross section.

Figure 5D:
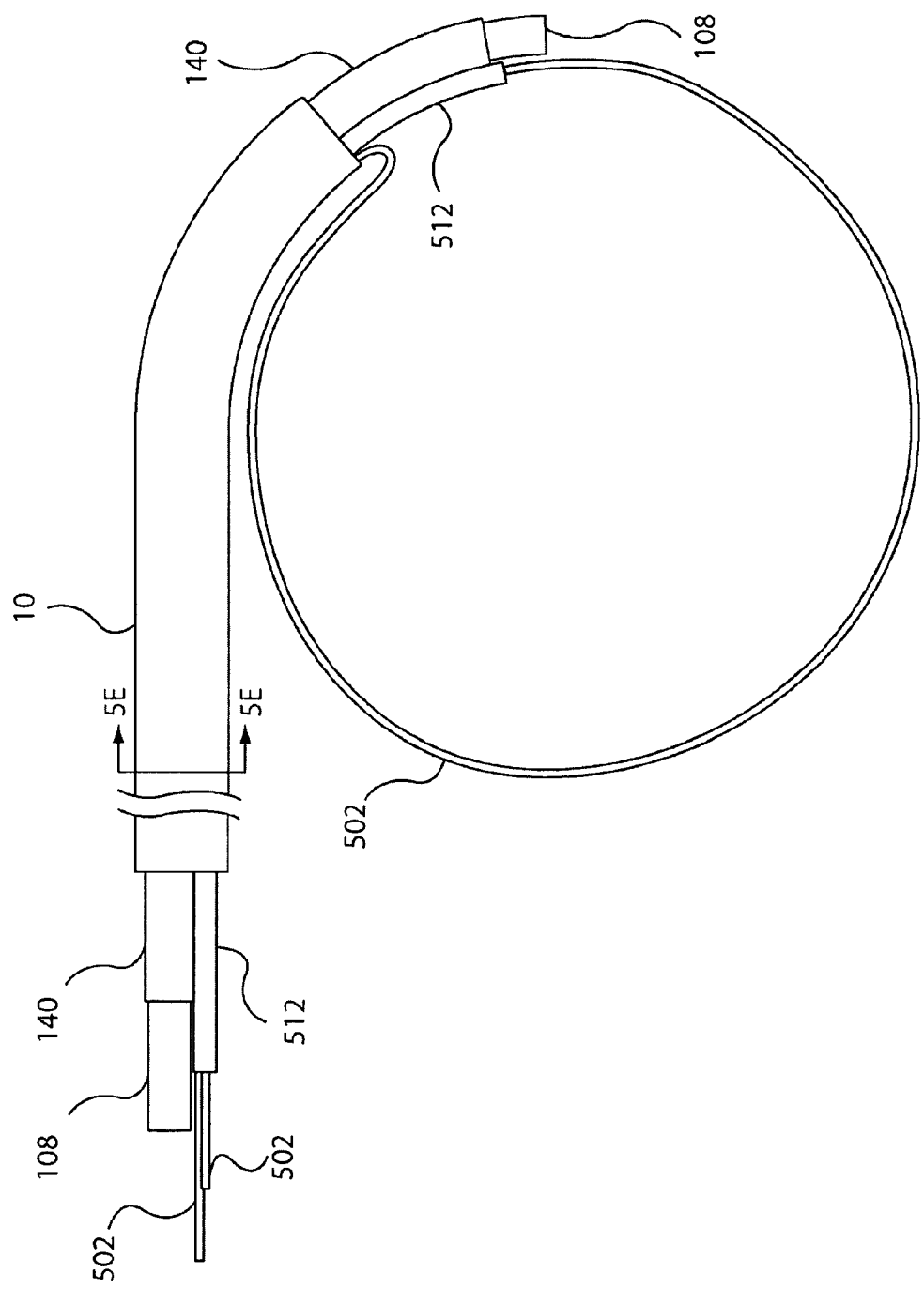
FIG. 5D-5E are a series of views depicting yet another embodiment of a delivery system in accordance with the present invention.

FIG. 5D shows a side view of another embodiment of a delivery system comprising a looped rail that can be used to deliver a sheath to the anatomy. In the embodiment shown, functional device 108 is a sheath that can be delivered by the delivery system. Functional device 108 encloses a lumen. Further functional device 108 may comprise one or more electrodes (not shown) which could be electrophysiological mapping electrodes, electrophysiological pacing electrodes or electrophysiological ablation electrodes. In a preferred embodiment, the distal-most region of functional device 108 is deflectable. This can be achieved by providing a pull wire attached to a distal region of functional device 108. Functional device 108 can be rotated around its axis. Functional device 108 can also be advanced or withdrawn. Functional device 108 is introduced into the anatomy through guide sheath 140 as shown in FIG. 5D. Guide sheath in turn is introduced into the anatomy through a trans-septal sheath 10. A hollow rail guide 512 is attached to the outer surface of guide sheath 140. One end of a looped rail 502 passes through rail guide 512. Looped rail 502 enters the anatomy through the distal tip of rail guide 512, forms a loop in the anatomy and enters the delivery system in the space between the outer surface of guide sheath 140 and the inner surface of transseptal sheath 10. This design allows guide sheath 140 to be advanced into the anatomy or withdrawn from the anatomy over looped rail 502 and through trans-septal sheath 10. Guide sheath 140 can also be torqued within trans-septal sheath 10.

In one embodiment, looped rail 502 comprises a preshaped loop. One or more ends of looped rail 502 can be torqued to define the shape of looped rail 502 in the anatomy. In one embodiment, one end of looped rail 502 is fixed. In this embodiment, the shape of looped rail 502 in the anatomy is changed by advancing or withdrawing the other non-fixed end of looped rail 502. The distal end of functional device 108 is navigated to the target region in the anatomy by one or more of advancing, withdrawing, or torquing one or both ends of looped rail 502, advancing, withdrawing, or torquing functional device 108, and/or advancing, withdrawing, or torquing guide sheath 140. One or more devices may then be introduced into the anatomy through functional device 108.

Figure 5E:
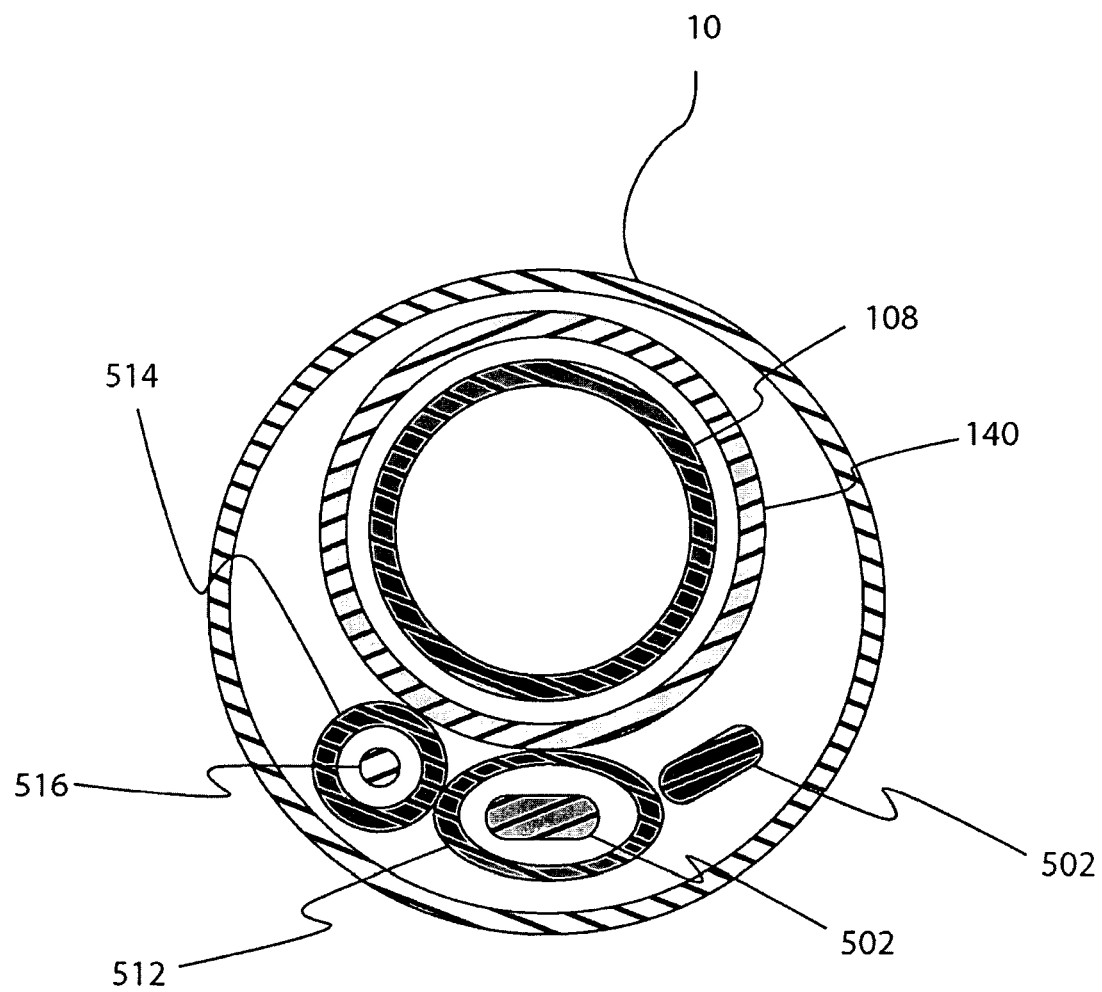

FIG. 5E shows a cross section through the delivery system embodiment of FIG. 5D through the plane 5E-5E. FIG. 5E shows outer trans-septal sheath 10 enclosing guide sheath 140 which in turn encloses functional device 108. Attached to the outer surface of guide sheath 140 are two tubes containing lumens: rail guide 512 and a pull-wire guide 514. Rail guide 512 and pull-wire guide 514 are attached to the outer surface of guide sheath 140 by discrete ties. In an alternate embodiment, rail guide 512 and pull-wire guide 514 are attached to the outer surface of guide sheath 140 by over-molded pieces or one or more pieces of heat shrink tubing. This combination of rail guide 512, pull-wire guide 514 and guide sheath 140 reduces the surface area of contact between the outer surface of the combination and the inner surface of trans-septal sheath 10. This in turn reduces the friction between the combination and trans-septal sheath 10. Rail guide 512 encloses a region of looped rail 502. Another region of looped rail 502 passes through the region between the outer surface of guide sheath 140 and the inner surface of trans-septal sheath 10.

In the preferred embodiment shown, the cross section of looped rail 502 is substantially rectangular. In the preferred embodiment shown, the cross section of rail guide 512 is substantially elliptical. A pull-wire 516 passes through pullwire guide 514. Pull-wire 516 is used to deflect the distal end of functional device 108.

Figure 5F:
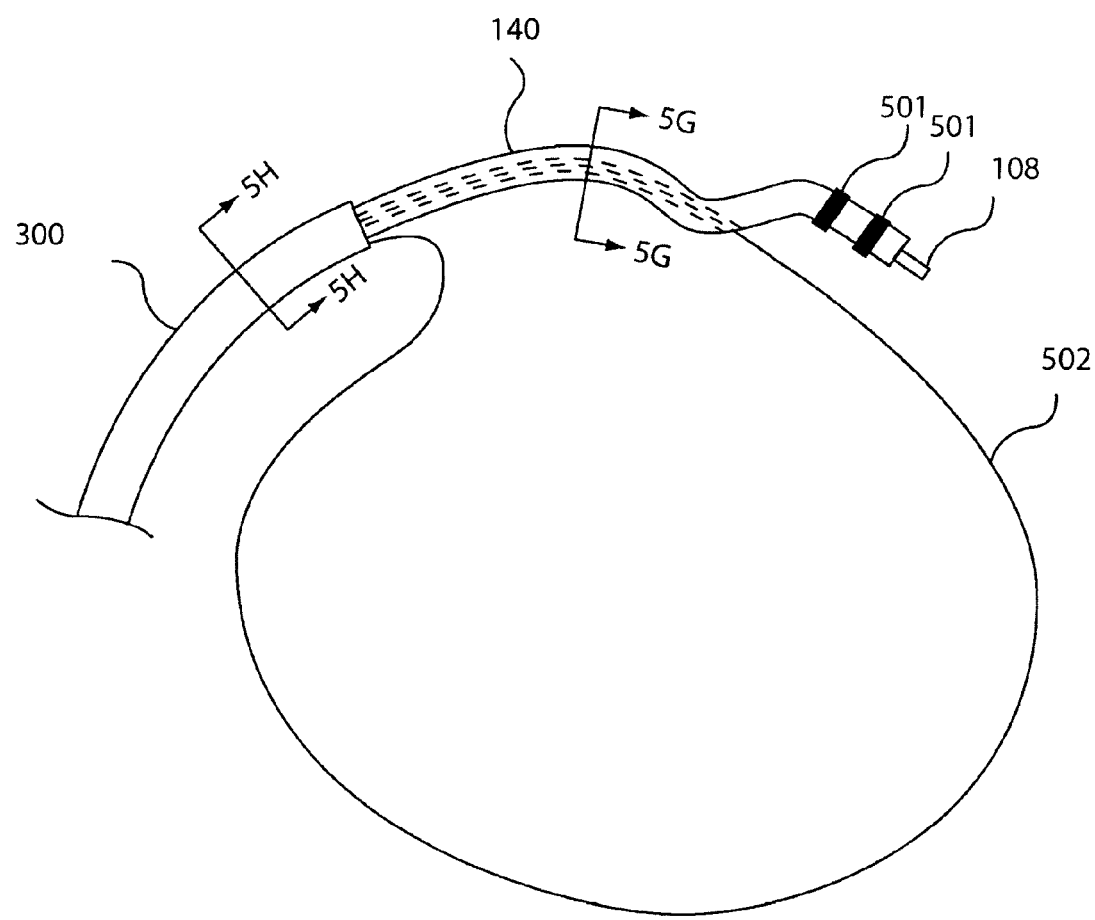
FIG. 5F-5H are a series of views depicting still another embodiment of a delivery system in accordance with the present invention, the positioning element having a preshaped distal portion.

FIG. 5F shows the side view of an embodiment of a delivery system for delivering a functional device through the lumen of a hollow guide sheath, wherein a proximal portion of the guide sheath is guided over a looped rail. In FIG. 5F, a proximal portion of guide sheath 140 passes over looped rail 502. The distal most region of guide sheath 140 is offset from the path of looped rail 502 as shown in FIG. 5F. The distal region of guide sheath 140 also comprises one or more electrodes 501. Electrodes 501 could be electrophysiological mapping electrodes, electrophysiological pacing electrodes or electrophysiological ablation electrodes. In the preferred embodiment, electrodes 501 are electrophysiological mapping electrodes. Guide sheath 140 is designed to enable the user to introduce one or more functional device 108, for example ablating devices, through one or more lumens of guide sheath 140. The proximal regions of guide sheath 140 and looped rail 502 are enclosed within trans-sepal sheath 10.

Figure 5G:
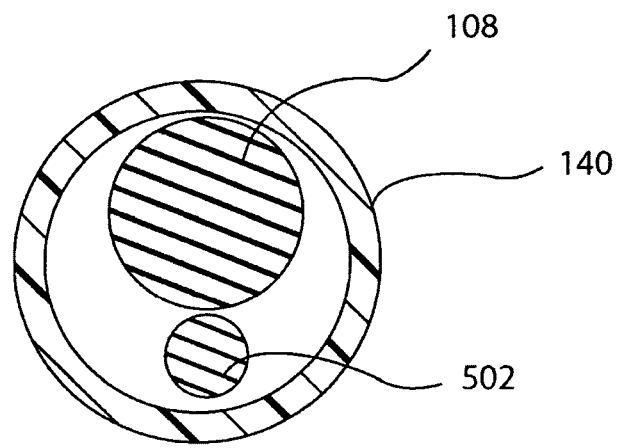

FIG. 5G shows the cross-section through the delivery system of FIG. 5F through the plane 5G-5G. In FIG. 5G, guide sheath 140 comprises a single lumen. The lumen of guide sheath 140 encloses functional device 108 and a region of looped rail 502.

Figure 5H:
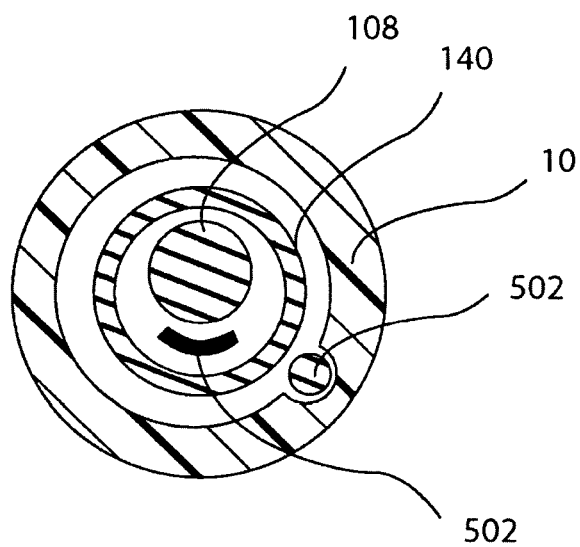

FIG. 5H shows the cross-section through an alternate embodiment of the delivery system of FIG. 5F through the plane 5G-5G wherein at least a portion of the looped rail has an arc shaped cross section. In FIG. 5H, trans-septal sheath 300 encloses guide sheath 140. In FIG. 5H, guide sheath 140 comprises a single lumen. The lumen of guide sheath 140 encloses functional device 108 and a region of looped rail 502. The region of looped rail 502 enclosed by guide sheath 140 has an arc shaped cross section. Such an arc shaped cross section allows looped rail 502 to preferentially loop such that the wider surface lies on the outer side of the loop and the narrower surface lies on the inner side of the loop. A region of looped rail 502 is enclosed between the outer surface of guide sheath 140 and the inner surface of trans-septal sheath 300. In the embodiment shown in FIG. 5H, the inner surface of trans-septal sheath 300 has an indentation to enclose looped rail 502.

Figure 5I:
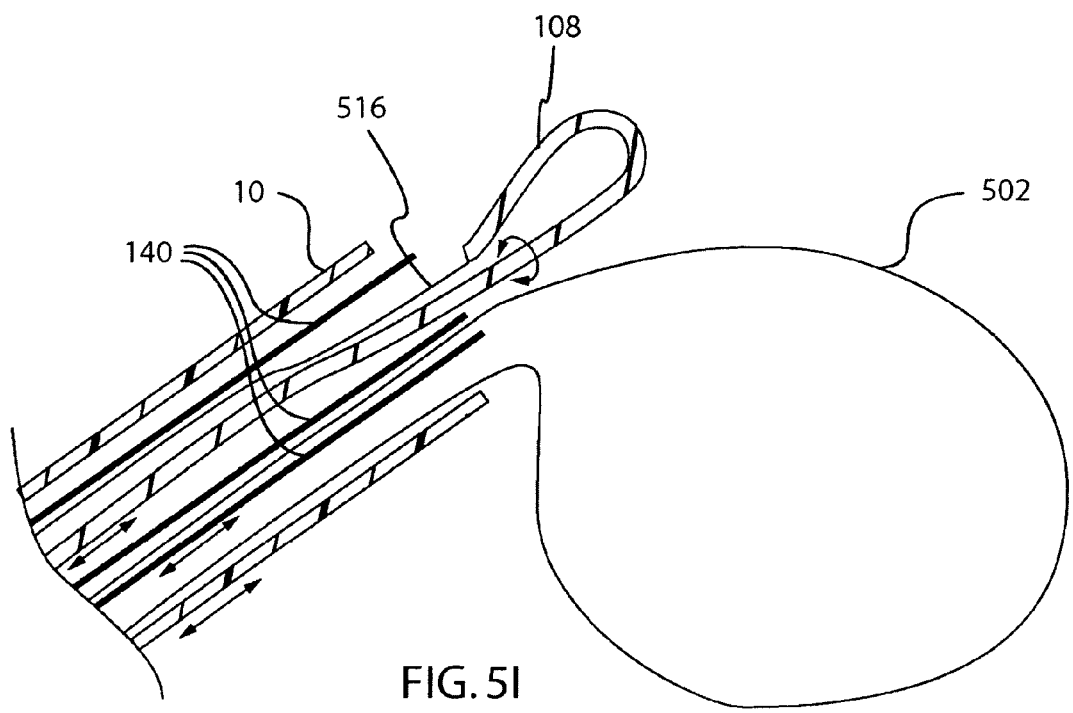
FIGS. 5I-5J are a series of views depicting another embodiment of a delivery system in accordance with the present invention.

FIG. 5I shows a view of an embodiment of a delivery system for delivering a deflectable, hollow functional device over a looped rail. In FIG. 5I, a guide sheath 140 is advanced through the lumen of a trans-septal sheath 10. In the embodiment shown, guide sheath 140 comprises two lumens: a first lumen for introducing a functional device 108 and a second lumen for introducing guide sheath 140 over a looped rail 502. Functional device 108 may comprise one or more electrodes which could be electrophysiological mapping electrodes, electrophysiological pacing electrodes or electrophysiological ablation electrodes. In a preferred embodiment, functional device 108 comprises one or more electrophysiological mapping electrodes. Functional device 108 is deflectable. In the embodiment shown, the deflecting mechanism is a pull wire 516. Pull wire 516 passes through the lumen of guide sheath 140 containing functional device 108. Pull wire 516 is pulled by the user to deflect the distal end of functional device 108. Looped rail 502 may be single stranded or multi-stranded. Looped rail passes out of guide sheath 140 through the second lumen of guide sheath 140, loops in the anatomy and enters the region between the outer surface of guide sheath 140 and the inner surface of trans-septal sheath 10. One or more ends of looped rail 502 can be pulled, pushed or torqued to adjust the position and/or the orientation of looped rail 502 in the anatomy. In a method embodiment, the distal end of functional device 108 is navigated to the target region in the anatomy by one or more of advancing, withdrawing, or torquing one or both ends of looped rail 502, advancing, withdrawing, or torquing functional device 108, pulling or releasing pull-wire 516, and/or advancing, withdrawing, or torquing guide sheath 140. One or more devices, for example ablation devices, may then be introduced into the anatomy via a lumen of functional device 108.

Figure 5J:
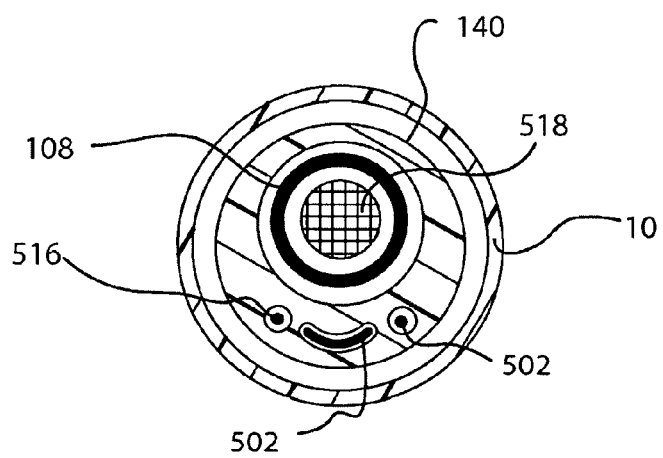

FIG. 5J shows a cross section through an alternate embodiment of a delivery system for delivering a deflectable, hollow functional device over a looped rail. In FIG. 5J, a guide sheath 140 is located in the lumen of a trans-septal sheath 10. In the embodiment shown, guide sheath 140 comprises four lumens: a first lumen for introducing a functional device 108, two lumens for holding two ends of a looped rail 502 and a lumen for holding pull wire 516. Such an arrangement of lumens reduces the overall profile of guide sheath 140. Pull wire 516 is attached to a distal region of functional device 108. Pull wire 516 can be pulled by the user to deflect the distal end of functional device 108. Functional device 108 may comprise one or more electrodes which could be electrophysiological mapping electrodes, electrophysiological pacing electrodes or electrophysiological ablation electrodes. In a preferred embodiment, functional device 108 comprises one or more electrophysiological mapping electrodes. Looped rail 502 may be single stranded or multi-stranded. Looped rail 502 passes out of guide sheath 140 through a lumen of guide sheath 140, loops in the anatomy and re-enters guide sheath 140 through another lumen of guide sheath 140. As shown in FIG. 5J, the cross section of looped rail 502 is variable along the length of looped rail 502. At least a portion of looped rail 502 that loops in the anatomy has an arc shaped cross section. Such an arc shaped cross section allows looped rail 502 to preferentially loop such that the wider surface lies on the outer side of the loop and the narrower surface lies on the inner side of the loop. In the embodiment shown in FIG. 5J, a device, for example an ablating device 518, is introduced through the lumen of functional device 108.

Figure 5K:
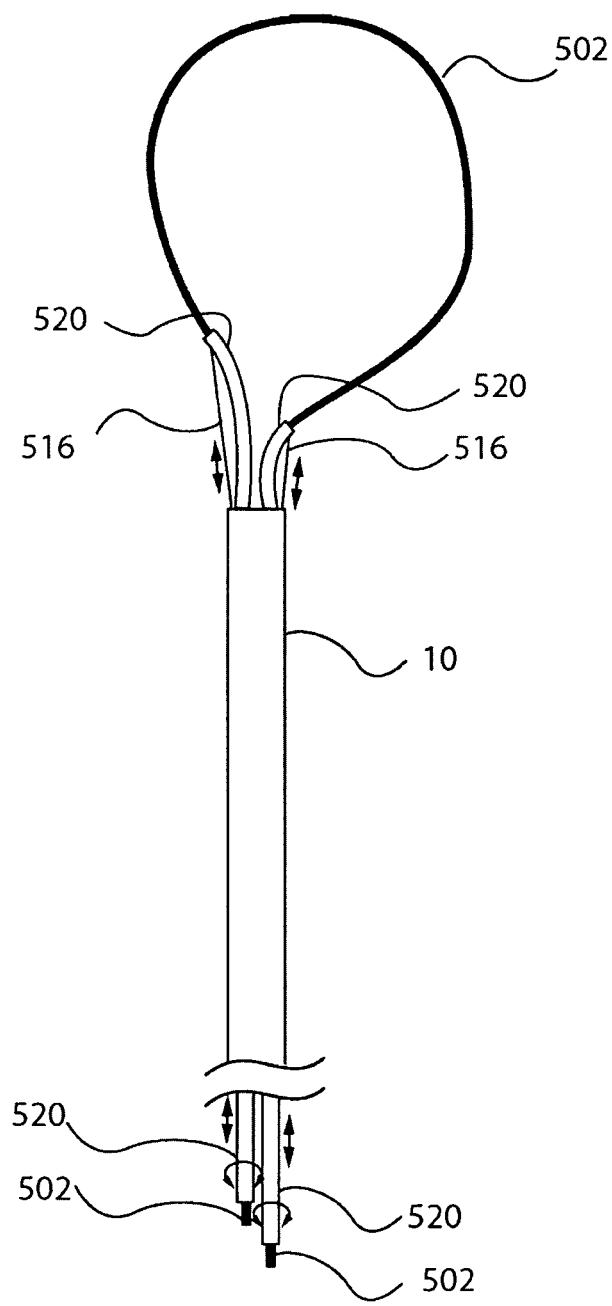
FIG. 5K-5M are a series of side elevation views of an alternative steering embodiment in accordance with one aspect of the present invention.

FIG. 5K shows a side view of an embodiment of a looped rail system for guiding one or more devices in the anatomy wherein one or more regions of the loop can be manipulated by one or more manipulating arms. In FIG. 5K, a trans-septal sheath 300 is used to introduce a looped rail 502 into the anatomy. In one method embodiment, looped rail 502 is introduced into the left atrium through trans-septal sheath 10 which passes through the Foramen Ovale (FO). It may be desired to adjust the position and/or the orientation of one or more regions of looped rail 502 in the anatomy. In one method embodiment, this is achieved by advancing, withdrawing or torquing the proximal ends of looped rail 502.

In the embodiment shown in FIG. 5K, two manipulating arms or hypotubes 520 are located over the ends of looped rail 502 as shown. Manipulating arms 520 pass through trans-septal sheath 10 and into the anatomy. Although the embodiment shown in FIG. 5K shows two manipulating arms 520, various embodiments of looped rail systems can be designed with only a single manipulating arm 520. In one embodiment, manipulating arms have pull wires 516, as depicted. One or both pull wires 516 can be pulled by the user to deflect the distal end of manipulating arms 520. Alternatively the manipulating arms 520 can be preshaped such that as then exit the distal end of introducer sheath 10 they take on the pre-shaped form. In a method embodiment using the system shown in FIG. 5K, the position and/or the orientation of one or more regions of looped rail 502 is modified by one or more of advancing, withdrawing, or torquing one or more ends of looped rail 502, advancing, withdrawing, or torquing one or more manipulating arms 520 and/or pulling/releasing one or both pull-wires 516.

As stated above, in an alternate embodiment, manipulating arms 520 have preshaped distal ends. In a method of using this alternate embodiment, the position and/or the orientation of one or more regions of looped rail 502 is modified by one or more of advancing, withdrawing, or torquing one or more ends of looped rail 502 and advancing, withdrawing, or torquing one or more manipulating arms 520. Looped rail 502 may be manipulated to an orientation wherein the plane of looped rail 502 significantly lies out of any plane containing the distal end of trans-septal sheath 10.

Figure 5L:
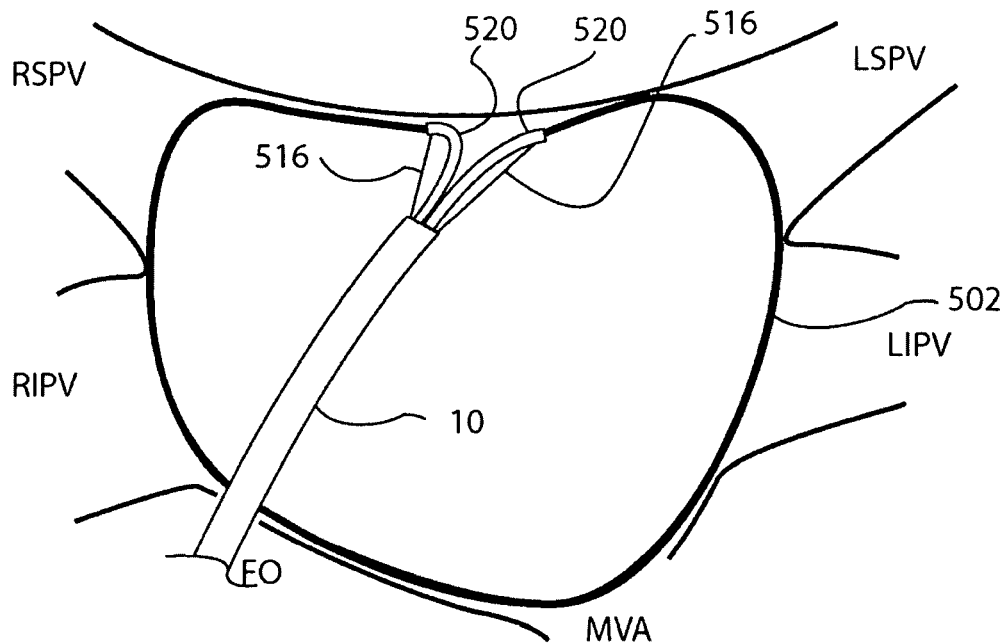
Figure 5M:
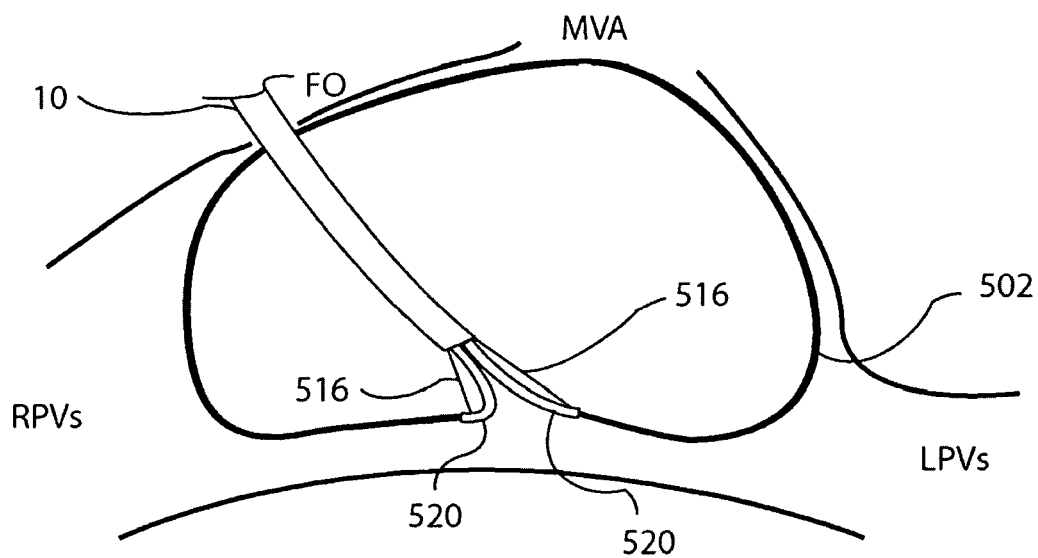

FIGS. 5L and 5M show two views of the embodiment of the looped rail system of FIG. 5K being used to create an access path to multiple regions in the left atrium. In the embodiment shown in FIGS. 5L and 5M, looped rail 502 is positioned such that looped rail 502 creates an access path to the Left Superior Pulmonary Vein (LSPV), Left Inferior Pulmonary Vein (LIPV), Right Superior Pulmonary Vein (RSPV), Right Inferior Pulmonary Vein (RIPV) and the Mitral Valve Annulus (MVA). Similarly, looped rail 502 can also be used to create an access path to the posterior wall of the left atrium. After creating a desired access path, one or more devices may be advanced over looped rail 502 in the anatomy.

Figure 6A:
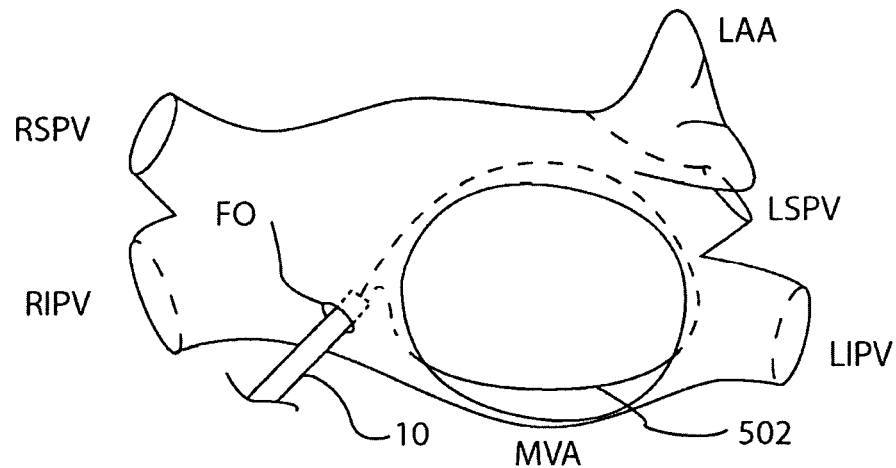
FIGS. 6A-6B are a series of perspective views, in partial cross-section, of the heart exemplifying a functional device being advanced therein via the embodiment of FIG. 5.

FIG. 6A shows a view of the left atrium of a human heart showing a looped rail being used to create an access path to the left pulmonary veins. In FIG. 6A, a trans-septal sheath 10 is introduced into the left atrium through the Foramen Ovale (FO). Thereafter, a looped rail 502 is introduced through trans-septal sheath 10. Looped rail 502 is manipulated such that a region of looped rail 502 is substantially adjacent to left pulmonary veins. Thus looped rail 502 creates an access path to the left pulmonary veins. Thereafter, one or more devices may be advanced over looped rail 502 into the anatomy to perform one or more procedures in or near the left pulmonary veins.

Figure 6B:
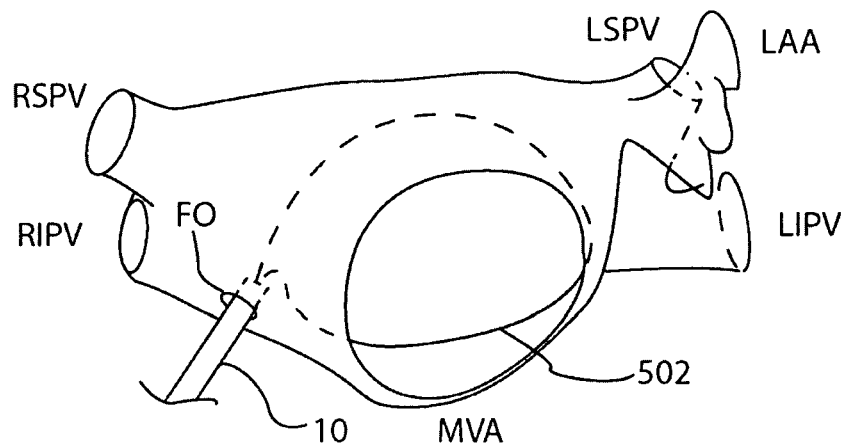

FIG. 6B shows a view of the left atrium of a human heart showing a looped rail being used to create an access path to the posterior wall of the left atrium and the region between the left inferior pulmonary vein and the Mitral valve annulus. In FIG. 6B, a trans-septal sheath 10 is introduced into the left atrium through the Foramen Ovale (FO). Thereafter, a looped rail 502 is introduced through trans-septal sheath 10. Looped rail 502 is manipulated such that a region of looped rail 502 is substantially adjacent to the posterior wall of the left atrium and another region of looped rail 502 is substantially adjacent to the region between the left inferior pulmonary vein and the Mitral valve annulus. Thus, looped rail 502 creates and defines an access or operative path to the posterior wall of the left atrium and the region between the left inferior pulmonary vein and the Mitral valve annulus. Thereafter, one or more devices may be advanced over looped rail 502 into the anatomy to perform one or more procedures at one of a plurality of positions relative to the operative path defined by rail 502 in or near the posterior wall of the left atrium and the region between the left inferior pulmonary vein and the Mitral valve annulus.

Figure 7:
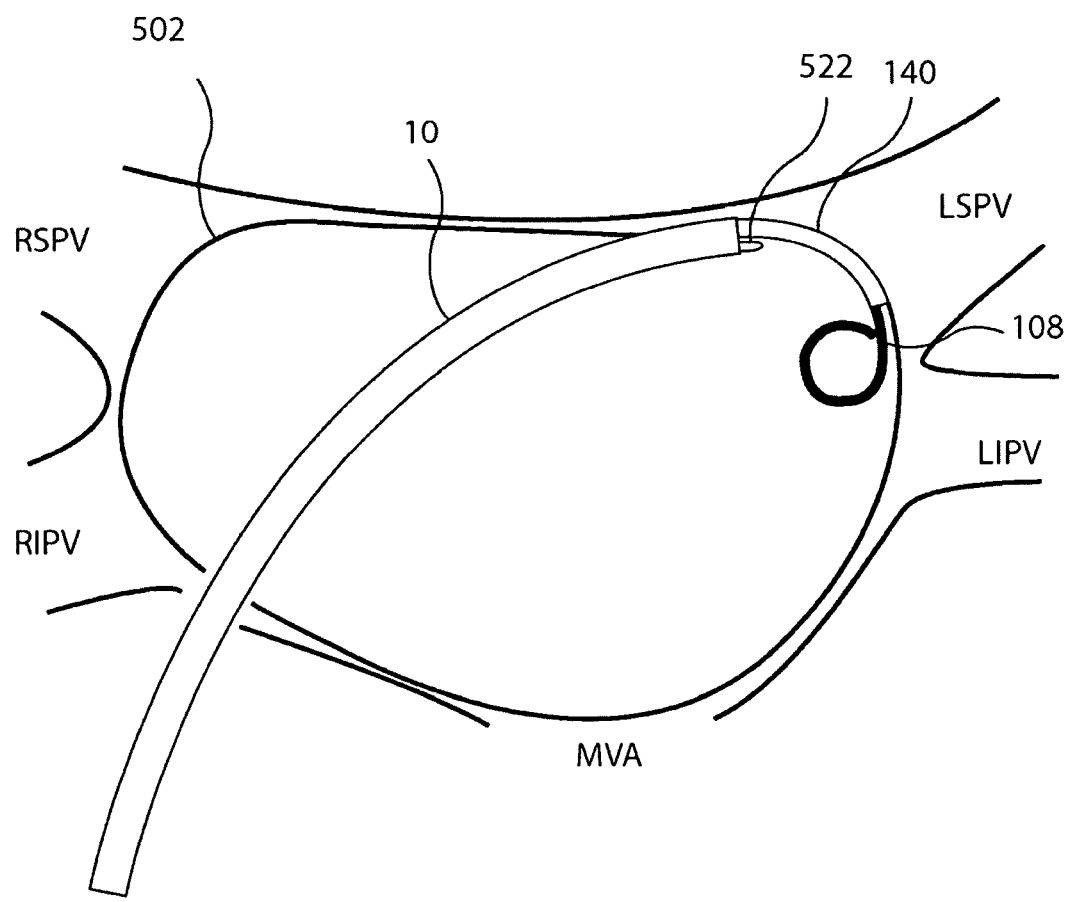
FIG. 7 is a side elevation view, in partial cross-section, of the heart exemplifying a functional device being advanced along an operative path via the embodiment of FIG. 5, the delivery system deployed within the pulmonary vein groove.

FIG. 7 shows a view of the left atrium of a human heart showing a looped rail being used to create an access path to multiple regions in the left atrium. In FIG. 7, a trans-septal sheath 10 is introduced into the left atrium through the Foramen Ovale (FO). Thereafter, a looped rail 502 is introduced through trans-septal sheath 300. Looped rail 502 is manipulated such that a region of looped rail 502 is substantially adjacent to multiple regions of the left atrium including Left Superior Pulmonary Vein (LSPV), Left Inferior Pulmonary Vein (LIPV), Right Superior Pulmonary Vein (RSPV), Right Inferior Pulmonary Vein (RIPV) and the Mitral Valve Annulus (MVA). Thereafter, one or more devices may be advanced over looped rail 502 into the anatomy to perform one or more procedures. In FIG. 7, a guide sheath is advanced over looped rail 502. A functional device 108 e.g. a mapping sheath is advanced through a lumen of guide sheath 140. Separately, an auxiliary device 522 is advanced through a lumen of trans-septal sheath 10. In a preferred embodiment, auxiliary device 522 is an imaging catheter.

Delivery System: Positioning Element Integral to Guide System

Now turning to FIGS. 8A-8C, another delivery system in accordance with the present invention will be discussed in greater detail. As shown, delivery system 300 comprises a guide system or rail 320 and positioning element 340, however in this case the positioning element 340 is adapted to be integral with rail 320, connected at their most distal points for example, at an interface point 344. Therefore, rather than the positioning element advancing over, or otherwise with respect to, the guide system itself, both the rail 320 and positioning element 340 are able to move in a coordinated and continuous manner along a defined operative path, as discussed in greater detail below.

As depicted, the positioning element 340 is fixedly attached to the guide rail 320 at the interface point 344. Such attachment can be achieved through any suitable fashioning means such as, for illustration purposes only, various methods used to weld or epoxy, or otherwise fixedly attach, the elements. Alternatively, the interface can be formed through a mechanically flexible joint such as a hinge member (not shown). Still yet, both the rail 320 and positioning element 340 can be formed from one continuous member, the item laser cut from a single piece of material for example, and then formed to give the positioning element its depicted tubular appearance. While preferably depicted as having a generally tubular body portion engaging the functional device at various points along its length, positioning element 340, as with other embodiments described herein, only needs to retain the functional device at least at one point. The retainment point defines the position relative to the operative path from which the functional device is deployed and also further provides an initial direction toward which the functional device is deployed.

Rail 320 includes a proximal control section which can be operated by a user directly or through operation of a control as part of a handle portion. Rail 320 preferably includes a rectangular cross-section to restrict the overall loop-shaped deployment of the rail 320 and positioning element 340 to a single geometric plane. In this way, more control is achieved with regard to the placement of the delivery system which, in turn, leads to more accurate placement of the functional device. The rectangular cross-section has suitable dimensions to allow for providing a stable platform from which the functional device can be deployed. The rectangular cross-section need not be present over the entire length of rail 320, however, is preferably present over that portion of rail 320 deployed past the introducer 10. Alternatively, the rail 320 could have a circular cross-section to provide for greater flexibility leading to improved steering of the deployed loop in various directions through a torsional force applied to a proximal control portion of the rail 320 as desired, discussed in greater detail below with respect to the operation of the delivery system 300.

Figure 8A:
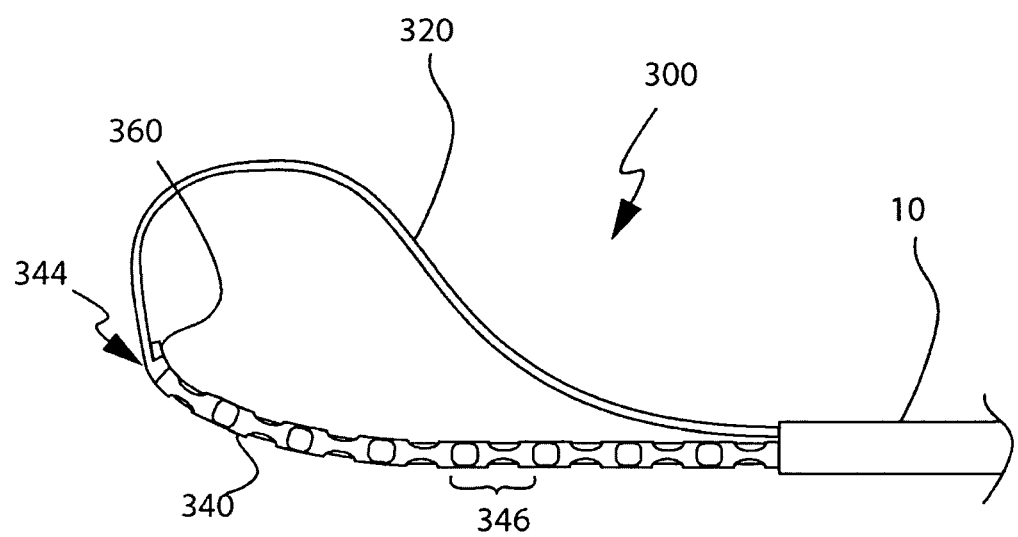

Turning now to FIGS. 8A and 8B, the positioning element 340, adapted to translatably and rotatably receive a functional device therethrough, will be discussed in greater detail. The positioning element 340, as with the rail 320, includes a proximal control section which can be operated by a user directly or through operation of a control as part of a handle portion. As discussed in greater detail below, the operation of the proximal control sections 322, 342 of the rail 320 and positioning element 340, respectively, are coordinated to allow for the deployment of the delivery system 300 to define an operative path, advancement of the positioning element along the path to define a position relative the path from which the functional device is deployed, as well as allowing the user the ability to reconfigure the path as desired during use.

As depicted, element 340 is generally a hollow structure defined by the interconnecting of a plurality of continuous sections 346. In one embodiment, each section 346 is formed by recessing or removing material from a tubular member defining a number of sections 346 consisting of structural members 348 interconnecting a plurality of ring type members 352 ending in ring member 350 at the interface point 344. Ring or retaining member 350 specifically defines a location along the operative path from which the functional device, alone or in combination with a delivery sheath, is deployed. Furthermore, the distal opening of ring member 350 defines at least one point of retainment for retaining a functional device as well as providing an initial direction toward which the functional device and/or a delivery sheath is deployed. As shown, the element 340 material is removed such that each structural member 348 pair is radially positioned 90° from its neighboring pair immediately distal and proximal thereto. Alternatively, element 340 could be formed from a series a rings arranged spaced apart from each other and connected through application of the structural member 348 pairs via welding or the like. Such a configuration allows for adequate flexibility of positioning element 340.

In either case, although each structural member 348 pair is shown having a length, generally equivalent to adjacent pairs, certain structural member 348 pairs can be adapted to have differing lengths to define correspondingly different flexibilities along the length of positioning element 340 to further encourage adaptation of the operative path for a specific medical procedure. In this way the positioning element can be designed to better match the general curvilinear inner surface of a hollow organ, such as the general curvilinear shapes associated with the left atrium of the human heart.

With specific reference to FIG. 8B, the positioning element 340 is adapted to balance the ability to receive the functional device therein while providing the requisite stability in support of the deployment of the functional device therefrom. This is achieved, in part, through the creation and arrangement of the structural members 348, as part of the sections 346. Each section 346 is approximately from about XX mm. to about XX mm. in length. Arranged as shown, the positioning element 340 has the ability to flex as it follows an operative path initially defined, for example, through deployment of the guide rail 320, as discussed in greater detail below.

The overall length of the positioning element 340 is at least as long as necessary to travel along the complete defined operative path of a desired length. A maximum length of about 20 cm. will be adequate for accessing most locations associated with many medical procedures, however positioning elements having longer lengths are contemplated for those procedures which require such access. The specific structure of the depicted positioning element 340 need not continue the complete length of the positioning element. Rather, the specific structure is preferably present on that part or portion of the positioning clement 340 which is deployed from introducer 10. However, only one retaining member is required to define the position along the operative path from which a functional device is deployed. Therefore, as a minimum, ring 350, or an element which provides similar retaining functionality, is required. Alternatively, the positioning element 340 can continue to the proximal control portion if desired.

Turning now to FIGS. 8A and 8C, in a preferred embodiment, the delivery system 300 also includes a delivery sheath 360 having a lumen 362 therethrough ending in a distal opening 364. Sheath 360 is slidably and rotationally positioned within the hollow longitudinal space of positioning element 340, as better depicted in FIG. 9B, and adapted to be deployed out the distal portion of the positioning element, ring 350 at the distal end of positioning element 340 for example. The delivery sheath 360 includes a distal portion 366 which is deflectable to further position, or otherwise steer, the functional device toward a target tissue area. The distal portion 366 may be of a given length generally ending at a point along the sheath identified and depicted by exemplary point 368, preferably the distal portion 366 having a flexibility greater than that of the remaining portion of sheath 360 in order to encourage a desired deflection of the distal portion 366.

The deflectability of the distal portion 366 of delivery sheath 360 can be achieved through any suitable means. For example, the distal portion can be preshaped, the distal portion 366 having a flexibility less than that of the positioning element 340 such that the distal portion 366 takes on its preshaped form as it exits the distal end of the positioning element 340. Alternatively, the delivery sheath 360 can include a steering mechanism such as one or more pull wires 361, as depicted in FIG. 8C, attached to the distal end of the sheath 360. Application of a tensile force upon the pull wire 361, via a control on a handle portion for example (not shown), results in deflection of the distal portion 366 of the sheath 360. The flexibility along the length of the sheath 360 can be uniform or, alternatively, predetermined such that upon application of the pull wire 361 the sheath 360 is adapted to deflect at one or more desired locations along that portion of the sheath 360 which extends out the distal opening 364. Utilizing such a pullwire steering system, it is preferable that the distal portion 366 of the delivery sheath 360 has the ability to return to a normal orientation once the tensil force associated with the pullwire 361 is removed. While shown external to sheath 360, the pull wire 361 can be positioned within sheath 360 if desired.

The delivery sheath 360 may include other elements suitable for the performance of a particular procedure. For example, the sheath 360 may include one or more electrodes 370 spaced along its distal portion 366 as depicted in FIGS. 8C and 8D, the electrodes 370 adapted to transmit and/or receive electrophysiological signals to and from a target tissue location, respectively. Such signals would be helpful, for example, to assess the efficacy of an ablation procedure as well as to assist in the determine of where such an ablation should occur.

As stated above, delivery sheath 360 is preferably slidably and rotatably positioned within positioning element 340. In this way, the distal portion 366 of the delivery sheath 360 can exit out the distal opening 364 of sheath 360, be deflected if desired, and then rotated with respect to the positioning element 240. Such cooperative movements provide increased flexibility in positioning a functional device with respect to an operative path defined through cooperative deployment of the guide system 320 and positioning element 240.

The delivery sheath 360 comprises a lumen 362 adapted to slidably and rotatably receive a function device, such as an exemplary ablation device 302 of FIG. 8D. As generally depicted in FIG. 8D, ablation device 302 has a generally planar loop-shaped ablating distal portion 308 ending in a distal end 104. As discussed in greater detail below, such an ablating portion, when placed upon or adjacent a target tissue location with the planar surface of the ablating portion 308 generally parallel to the tissue surface, ablating portion 308 creates an area ablation generally confined by the outer boundary of its loop-shape structure. Moreover, such an ablating portion 308 is further advantageous since, along with the deflected distal portion of the delivery sheath 360, its shape defines an offset distance with respect to the rail allowing the development of a torsional force therebetween, ultimately leading to greater tissue contact as between the ablating portion 308 and a target tissue surface.

The distal portion 308 of ablating device 302 is preferably preshaped having a flexibility less than that of the delivery sheath 360 such that as the distal end 304 of the device 302 exist the distal opening 364 of the sheath 360, the ablating device 302 takes on its preshaped form. As with other preshaped elements disclosed herein, such predetermined shapes can be created through any suitable means including, but not limited to, the use of memory retaining metals such as Nitinol or other shape retaining biological compatible metals or plastics.

Now turning to FIG. 9, operation of delivery system 300 will be discussed in greater detail. As specifically shown in FIG. 9A, an introducer 10 may be used to provide an initial positioning point from which to deploy the delivery system 300. Introducer 10 is adapted to include a lumen therethrough which slidably and rotatably receives the delivery system 300 therein. The distal end of delivery sheath 360 is depicted past the distal end of the positioning clement 340 for illustrative purposes only. The delivery sheath 360 may be initially positioned proximal the distal opening of the positioning element 340. Indeed, it may be desirable to retain the delivery sheath completely within the positioning element 340 during a given medical procedure, only the functional device being deployed distal to the distal opening of the positioning element 340, for example.

Figure 9A:
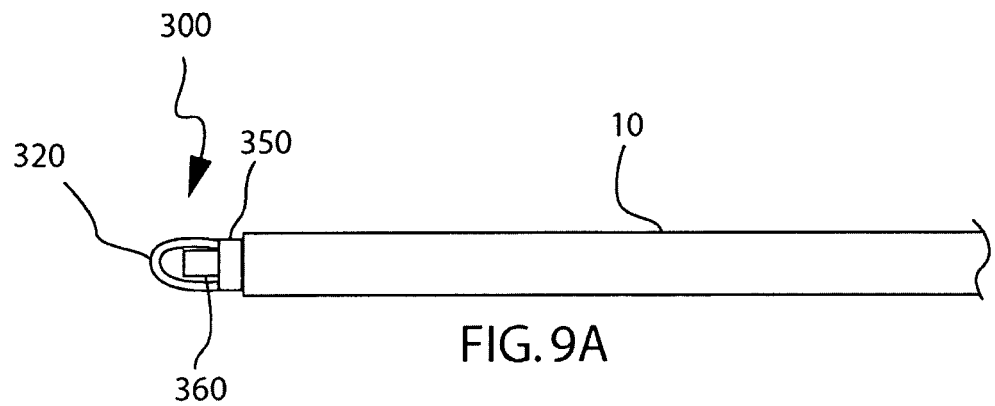
FIG. 9A-9D are a series of elevation views depicting an exemplary deployment of the delivery system of FIG. 8.
Figure 9B:
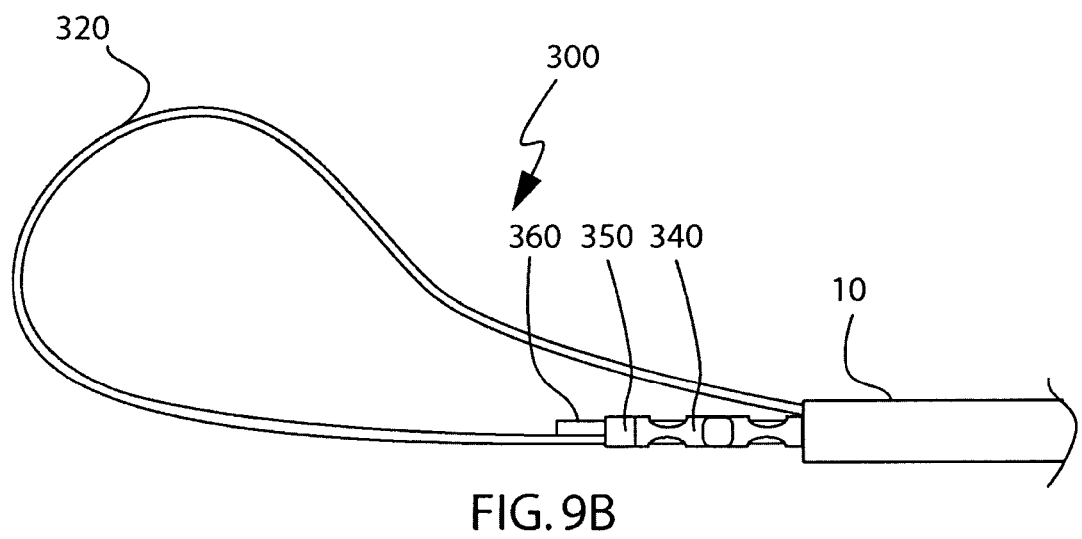

Advancing the proximal control section 322 of the guide rail 320 along or in combination with the proximal control section 342 of the positioning element 340 results in the deployment of the delivery system 300, that portion of the delivery system 300 exiting the distal opening of introducer 10 defining a loop-shaped operative path, as generally depicted in FIG. 9B. Again, the partial deployment of delivery sheath 360 past the distal end of guide member 340 is shown for illustrative purposes only. It should be apparent that if the proximal control portion 342 of positioning element 340 is advanced during deployment of delivery system 300, such advancement will result in the definition of an initial position along the operative path from which a functional device can be deployed.

If desired, continued deployment of the delivery system 300 can be made until the deployed delivery system 300 engages tissue along a majority of its length, providing additional stability for the deployment of the functional device as well as the delivery sheath 360 if applicable.

At this point, applying equal but opposing translatably forces to the proximal ends of the guide rail 320 and positioning element 340 will act to translate the distal ring member 350 of positioning element 340 along the defined operative path, the distal opening of the ring member 350 further defining a position along the path from which the delivery sheath and/or the functional device would be deployed. In this way, once the operative path is defined, the distal end of the positioning element 340 can be repeatably positioned at any location along the path. This is advantageous since some medical procedures, such as certain ablation procedures requiring the creation of long lesions within the left atrium of the heart, may require reapplication of a single ablation at a given location or position along the operative path as part of such a desired long lesion line. The present invention allows for such repositioning to occur in a quick, reliable and accurate manner, reducing procedural time, and ultimately procedure costs.

Figure 9C:
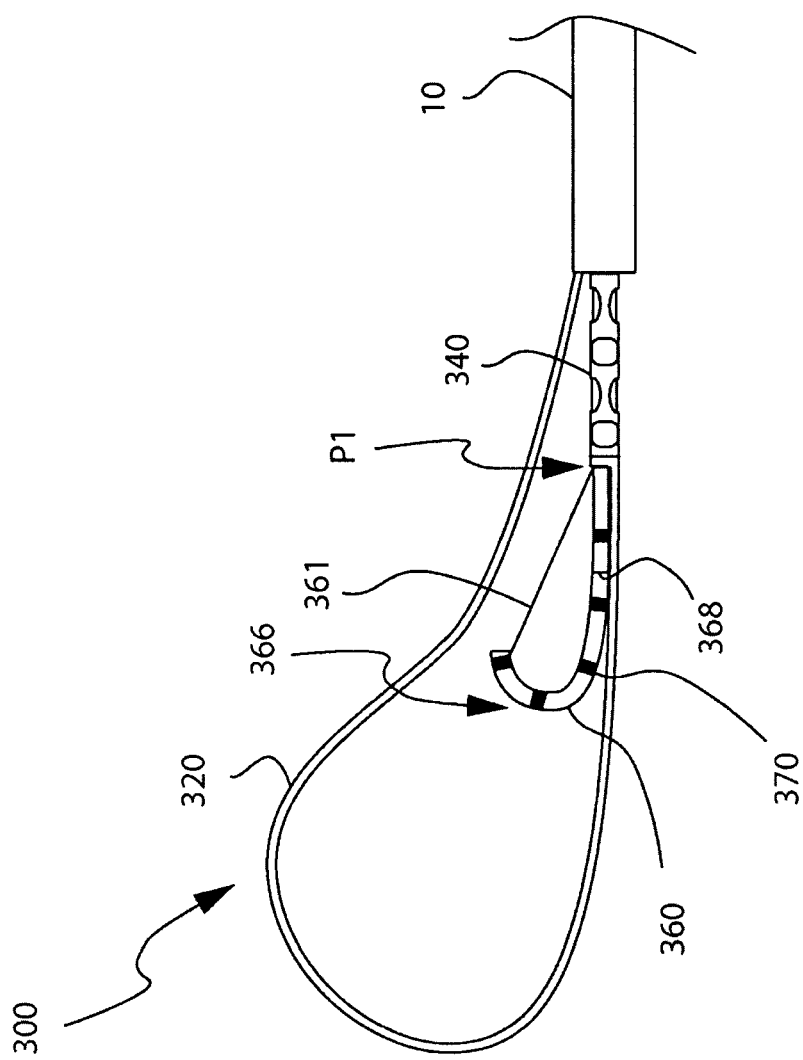

With respect to FIG. 9C, an exemplary deployment of the delivery sheath 360 from a position P1 along the operative path defined by the distal end of the positioning element 360 is depicted. Distal portion 366 of sheath 360 is defined in this depiction to include that distal portion extending from the distal opening of the sheath 360 and continuing to a transition point 368 along the sheath 360. Preferably, but not required, the flexibility of the distal portion 366 being less than that of the remaining portion of the sheath 360 to encourage deflection along the distal portion 366 only. Such a configuration is depicted for illustration purposes only and is not meant to be limiting. For example, the complete sheath 360 can be formed from material having a uniform flexibility along its entire length.

The distal end of delivery sheath 360 is advanced out the distal opening of the positioning element 340 a desired distance and then a tensile force is applied to a proximal portion of pull wire 368 to facilitate a desired deflection of the distal portion 366. It should now be apparent that through cooperative but opposing movement of the proximal control section 322 of the guide rail 320 and proximal control section 342 of the positioning element 340 would result in a corresponding translation of the position along the defined operative path from which the delivery sheath is deployed. Moreover, such an operation would result in a corresponding movement of a position defined by the distal opening of the sheath 360 relative to the operative path. By knowing the orientation of the distal portion 366 of sheath 360 with respect to the positioning element 340 and, more specifically, the distal end 350, a position relative to the defined operative path is defined by the distal opening of sheath 360. To assist in determining such an orientation of the distal portion 366, pull wire 361 may be operated by a translating control, as part of a handle portion for example (not shown), which can move from one position to another position amongst a plurality of defined positions. At each position the pull wire 361 control locks to that location, through the use of detents or frictional locking members, or the like for example, to allow the user to move from one position to another position, accurately and reliably able to advance to or return to any position relative the operative path.

Figure 9D:
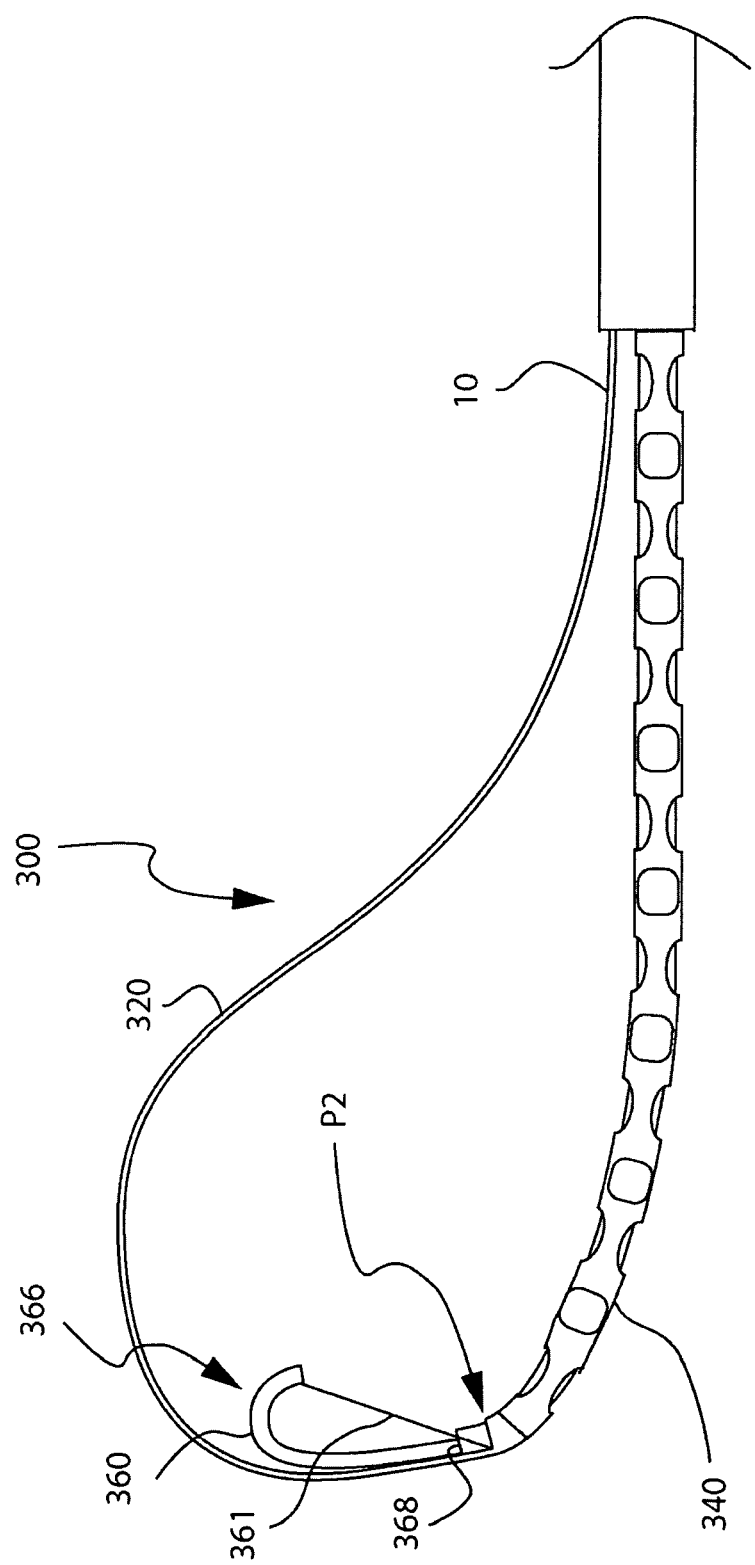

As depicted in FIG. 9D, the distal opening of sheath 360 is maintained at a known relationship or offset with respect to a second exemplary position P2 along the operative path defined by the guide rail 320 and positioning element 340 as part of the deployed guide system 300. In this way, with the loop-shape of the delivery system 300 placed adjacent and parallel to a desired target tissue, a medical procedure, such as an ablation procedure, can be accurately and reliably performed at a series of positions relative to the defined operative path. For example, the series of positions collectively can define an ablation line as part of a desired ablation pattern within a patient's heart. Alternatively, the loop-shape of the delivery system 300 can be expanded to substantially contact the inner surface of a hollow organ. The delivery sheath 360 can then be deployed as discussed above, and rotated such that the distal opening of the sheath 360 is positioned adjacent the inner surface of the hollow organ. It should be apparent that through additional coordinated movements of the proximal control sections 322, 342 of the guide rail 320 and positioning element 340, as discussed above, would result in the movement of the distal opening of the delivery sheath 360 along a series of positions along the inner surface of the hollow organ, the positions relative to the defined operative path.

Now turning to FIG. 10, an exemplary functional device in the form of ablation device 30 will be discussed in greater detail. As discussed below, ablation device 30 is adapted to be deployed out the distal opening of positioning element 340 or, more preferably, out the distal opening of delivery sheath 360. As generally depicted in FIGS. 10A-10C, ablation device 30 comprises a transmission line 31 ending in a preshaped ablating portion 32 adapted to emit electromagnetic energy therefrom. As best viewed in FIG. 10B, the transmission line includes a center conductor 33 surrounded by a layer of dielectric material 34. An outer conductor 36 surrounds the dielectric material 34 and is, in turn, surrounded by a suitable covering or jacket 38. The relationship of the various components of the transmission line 31 allow for the transmission of an electromagnetic signal to be transmitted from an energy source (not shown) to the ablating portion 32 and, ultimately, to a radiating portion 40, the electromagnetic energy being transmitted at a frequency greater than about 300 MHz.

The radiating portion 40 is defined by removing the outer jacket 38 and outer conductor 36 from a distal portion of the transmission line 31. Therefore, with reference to FIG. 10C, what is remaining from the transmission line along the ablating portion 40 is the center conductor 33 and the surrounding dielectric material 34. The length of the radiating portion 40 is selected such that the radiating portion 40 cooperates with the remainder of the ablating portion to provide the desired distribution of electromagnetic energy about the ablating portion 32, the ablating energy generally confined to the outer boundary of ablating portion 32. Therefore, with the ablating portion 32 placed upon a target tissue, the loop-shaped ablating portion placed adjacent and parallel to the target tissue, a lesion is created therein. The lesion consists of a surface lesion upon the target tissue surface generally corresponding to the shape of the ablating portion 32, continuing to a tissue depth proportional to the applied power of the electromagnetic energy. Other exemplary ablating portions are described in the co-pending application entitled, "ABLATING DEVICES AND METHODS FOR ABLATING BIOLOGICAL TISSUE", filed on Oct. 30, 2006, the disclosure of which is incorporated by reference in it's entirety.

Figure 10A:
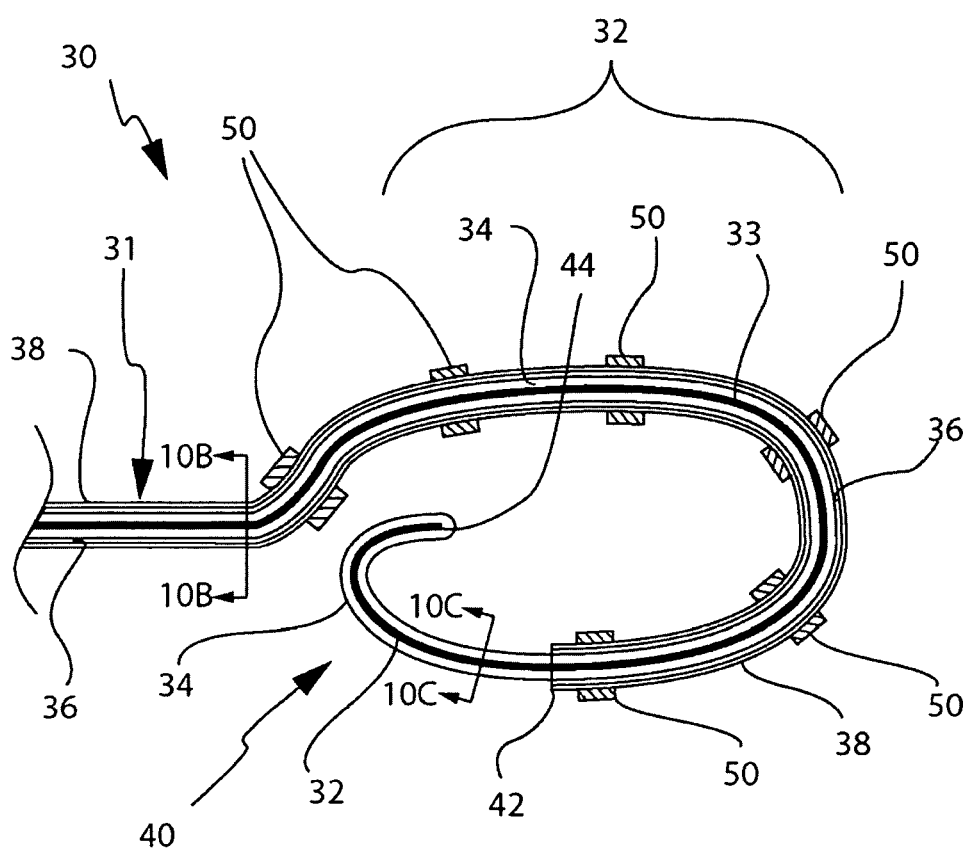
FIG. 10A is a planar view of an exemplary ablation device, in partial cross-section, used with the delivery system of FIG. 8.
Figure 10B:
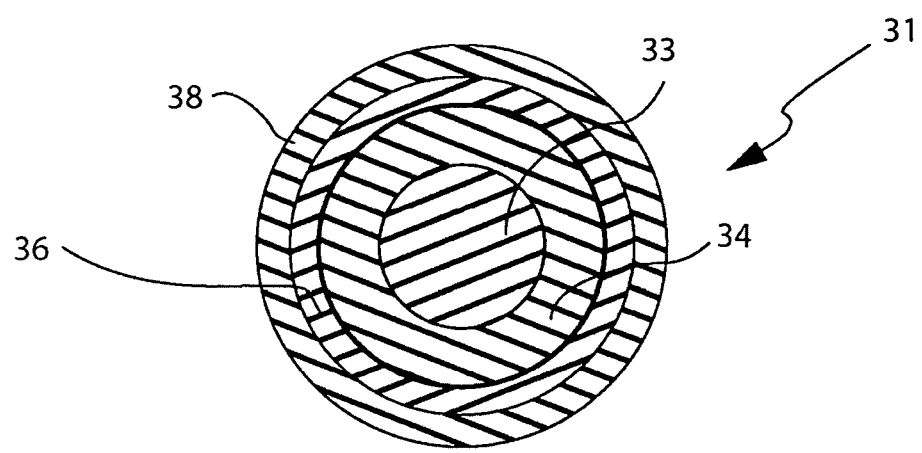
FIGS. 10B-10C are a series of cross-sectional views along the length of the exemplary ablation device of FIG. 10A.
Figure 10C:
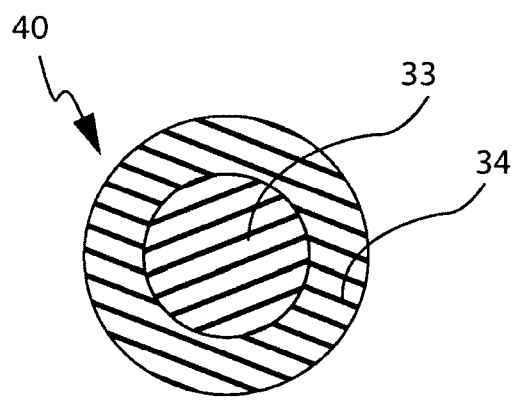

As depicted in FIG. 10A, the ablating portion 32 can include one or more electrodes 50 along its length. The electrodes can be used for the transmission and reception of various electrophysiological signals to and from the target tissue, respectively. For illustration purposes only, the electrodes 50 can be used along or in combination to determine where an ablation is to occur through mapping of undesirable electrical signals in the target tissue associated with cardiac arrhythmias. Alternatively, the electrodes 50 can be used alone or in combination to determine when an individual ablation is complete or where a subsequent lesion should be created such that the subsequent lesion is continuous with the previously created lesion.

More specifically, with regards to the creation of a desired lesion using ablating device 30, as the lesion is formed through application of electromagnetic energy to the ablating portion 32, since the lesion is generally confined by the geometric structure of ablating portion 32, the point when the desired lesion is created can be determined. For example, electrodes 50 can each be conveying electrical cardiac activity to the user. When electrical cardiac activity is no longer obtained from the electrodes 50, there is an absence of electrical signals received from the electrode 50 for example, the desired ablation corresponding generally to the ablating portion 32 has been created.

Thus, through placement of the ablating portion 32 upon a target tissue at a first position a first ablation can be created. Since delivery system 300, as with other embodiments herein, allow for the deployment of a functional device, such as ablation device 30, at one or more known positions relative to a defined operative path, through simple translational movements a subsequent second lesion continuous with the first can be created by ablating device 30. As the ablating portion 32 is translated, or otherwise moved, relative the operative path, cardiac electrical signals can be acquired via electrodes 50. As ablating portion 32 is moved from the site of the first ablation, one or more electrodes 50 will contact non-ablated cardiac tissue, the non-ablated cardiac tissue able to communicate cardiac electrical signals to the one or more electrodes 50. In this way, the ablating portion can be moved until only one or two electrodes 50 are electrically silent, indicating they are still positioned atop the first ablation. At this point the current position of the ablating portion 32 can be maintained and the subsequent lesion created, such subsequent lesion being continuous with the first.

Figure 11A:
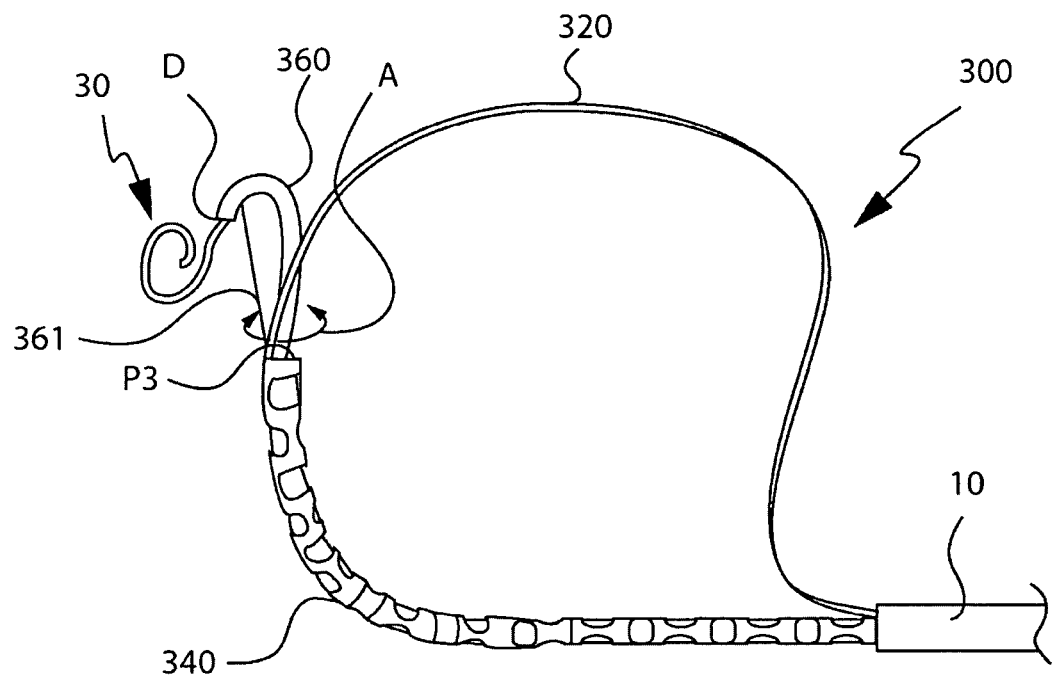
FIGS. 11A-11B are perspective views of the delivery system of FIG. 8 depicting the deployment of the exemplary ablation device of FIG. 10.
Figure 11B:
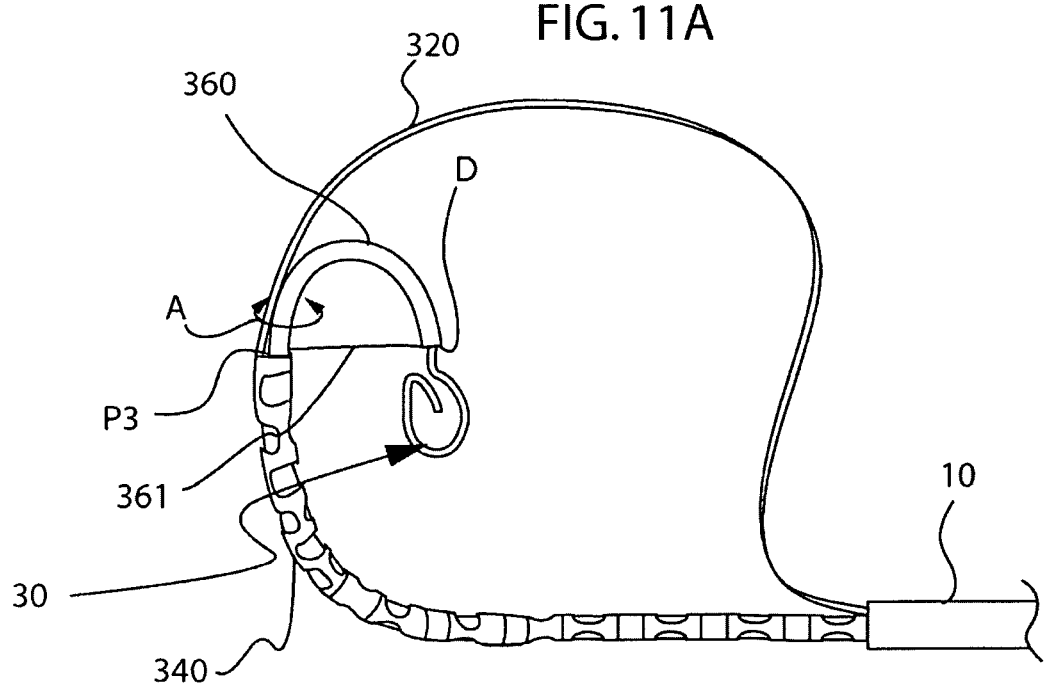

FIGS. 11A and 11B depict rotational placement of the delivery sheath 360 about and relative to another exemplary position P3 along the operative path defined by the delivery system 300. As discussed above, the guide rail 320 and positioning element 340 are integral in the delivery system 300 embodiment. FIGS. 11A and 11B depict the deployment of the guide rail 320 and positioning element 340 defining an operative path with respect which a functional device can be deployed. More specifically, the distal end of positioning element 340 defines a position P3 along the operative path, while the distal opening of delivery sheath 360 defines a position relative the operative path, functional device 30 depicted being deployed from the distal end of delivery sheath 360. As discussed in greater detail above, pull wire 361 can be used to define the distal position D relative the operative path from which the functional device is deployed.

As previously discussed, as well as being translatable with respect to the delivery system 300, delivery sheath 360 is also rotatable with respect to delivery system 300, such movement generally indicated by arrow A in FIGS. 11A and 11B. FIG. 11A depicts a first of a plurality of exemplary orientations of delivery sheath 360 and functional device 30 exiting therefrom to address a first target tissue location. FIG. 11B depicts a second of the plurality of exemplary orientations of delivery sheath 360 and functional device 30. It should be apparent that the combination of the delivery system 300 cooperating with the delivery sheath 360 and a functional device, such as device 30, provides tremendous stability and control over the positioning of the functional device with respect to a known operative path. This is buttressed by the fact that the functional device 30 is both translatable and rotatable with respect to the delivery sheath, and ultimately the delivery system 300 and the operative path which is defines.

Figure 12:
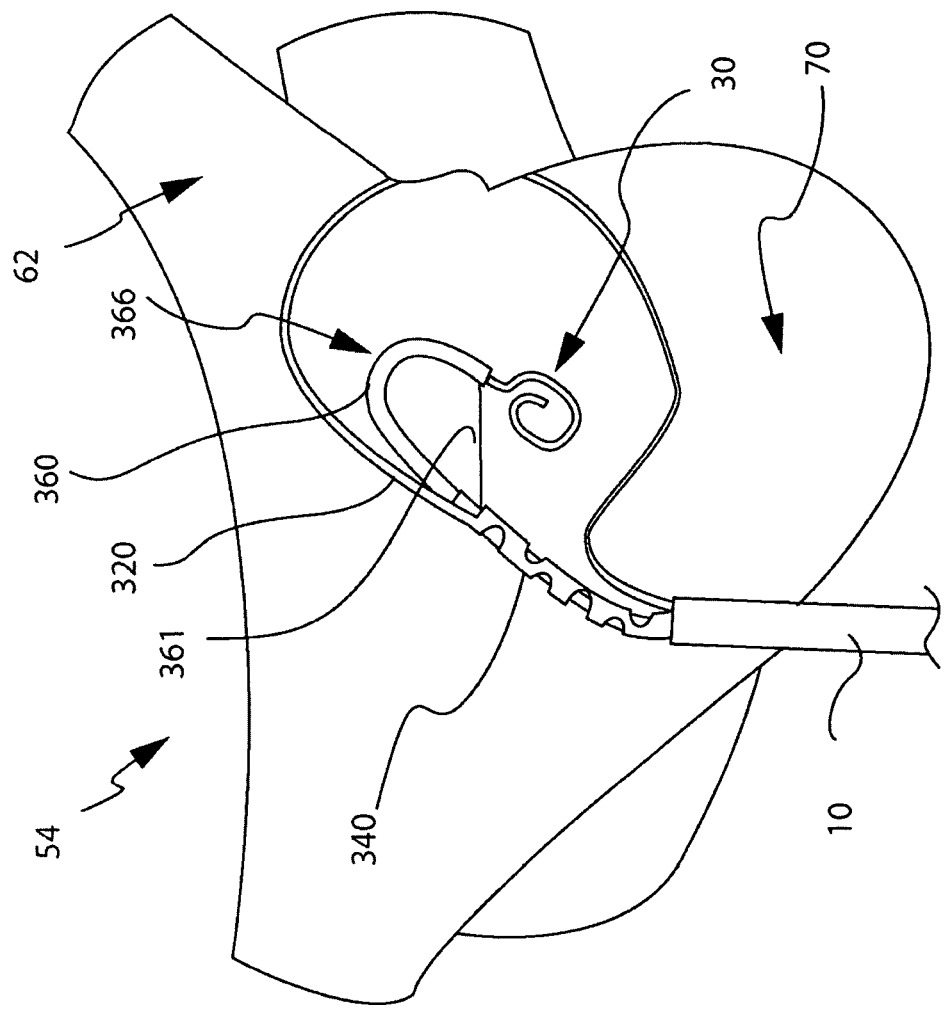
FIG. 12 is a perspective view depicting an exemplary placement of the system of FIG. 11 within the left atrium of a patient's heart.

With reference now to FIG. 12, a first exemplary placement of delivery system 300 within a left atrium 54 of a patient's heart will be discussed. As depicted, trans-septal sheath 10 is deployed across the septal wall of the heart, the distal end of the sheath 10 positioned within a left atrium 54 of the heart. The delivery system 300 is then deployed out the distal end of a sheath 10, as discussed in greater detail above. As depicted, the loop-shaped guide rail 320 is positioned within the pulmonary groove located at the ostia of the left pulmonary veins 62 of the heart, the guide rail 320 positioned over the ostia of the left pulmonary veins 62. In this way the functional device, ablating device 30 for example, has access to the atrial wall tissue which surrounds the pulmonary veins 62. The ablating portion 32 of device 30 can then be translatably and rotatably positioned at one or more positions with respect to the operative path defined by the placement of guide rail 320 to create a continuous lesion around the left pulmonary vein 62 ostia. It is important to note that the positioning of the rail 320 over the ostia of the left pulmonary veins 62 occurs independent of the specific nature of the ostia. More specifically, the specific anatomical structure of the pulmonary vein 62 ostia differs from one patient to another. For example, both of the left pulmonary veins 62 may interface to the left atrium 54 via a separate opening individual to each left pulmonary vein. Alternatively, the left pulmonary veins 62 may interlace with the left atrium 54 through a single common opening. Either way, the delivery system 300 will self-adapt to such anatomical differences allowing for the stable, accurate and reliable placement of the delivery system 300 close thereto and, ultimately, the functional device.

Another important feature the delivery system 300, as with other embodiments described herein, is the fact that such ablations, for example the continuous lesion created about the left pulmonary veins 62 described immediately above, are created through simple user inputs without requiring the redeployment of the delivery system 300 itself. Moreover, the delivery system 300 allows for the user to reposition the functional device 30 to perform additional ablations as required, as a result of a mapping procedure for example.

It should also be apparent that such placement of the delivery system 300 allows for creation of additional lesion lines as well. For example, with the delivery system 300 deployed within the left pulmonary vein 62 groove, the ablation device 30 can be further deployed, through manipulation of the delivery sheath 360 and ablation device 30, to create a continuous lesion joining the left pulmonary vein 62 ablation line and a mitral valve 70 leading from the left atrium 54 to the left ventricle (not shown).

Now with reference to FIGS. 13A through 13C, another exemplary placement of delivery system 300 will be discussed in greater detail. As depicted, the rail 320 is positioned within the pulmonary groove of both the left and right pulmonary veins, respectively. The pulmonary vein groove includes that area of tissue where the left and right pulmonary veins interface to the left atrium. The pulmonary vein groove provides added stability for the deployment of a functional device, ablation device 30 for example, and also properly defines an operative path P about which the ablation device 30 can be deployed in order to create a desired lesion pattern. As discussed above, deployment of the rail 320 over the pulmonary vein ostia provides access to the atrial tissue surrounding the pulmonary veins, thus providing the ability to create a corresponding lesion there around.

Figure 13A:
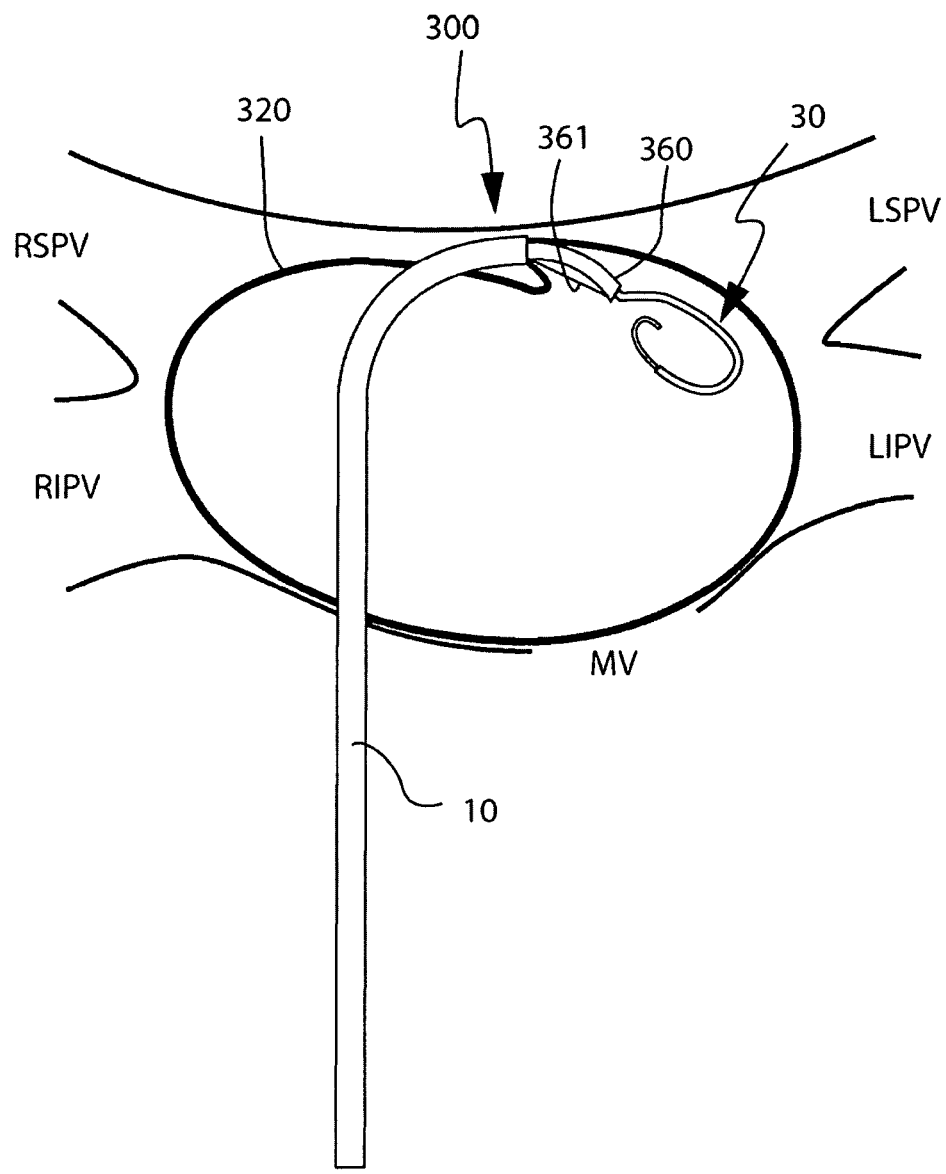
FIGS. 13A-13C are a series of side elevation views depicting the deployment of the ablation device of FIG. 10 at several positions within the left atrium of a patient's heart from an alternative embodiment of the delivery system of FIG. 8.

Once the rail 320 is positioned within the pulmonary vein groove either the ablating device 30, the delivery sheath 360, the positioning element 340, or a combination thereof, can be deployed to create a first ablation as part of a series of ablations forming a desired lesion pattern, as generally depicted in FIG. 13A. The positioning element 340, delivery sheath 360, ablation device 30, or a combination thereof, are then further deployed as desired to position the ablating device 30 at a second ablation site and third ablation site as generally depicted in FIGS. 13B and 13C. For creating ablations around the left pulmonary veins 62 as generally depicted in FIG. 13, an ablation site is selected on one lateral side of the left pulmonary vein ostia. Once the ablation is created, the delivery sheath 360 can then be rotated with respect to the positioning element 340 and a second lesion on the opposing side of the left pulmonary vein ostia can then be created. Once mirroring ablations are created about the left pulmonary veins at a given position relative the operative path, the ablating device 30 is then advanced to another location relative to the operative path, through operation of the various elements of the delivery system 300 as discussed herein, and the further creation of various additional ablations as part of a desired lesion set are created.

Figure 13B:
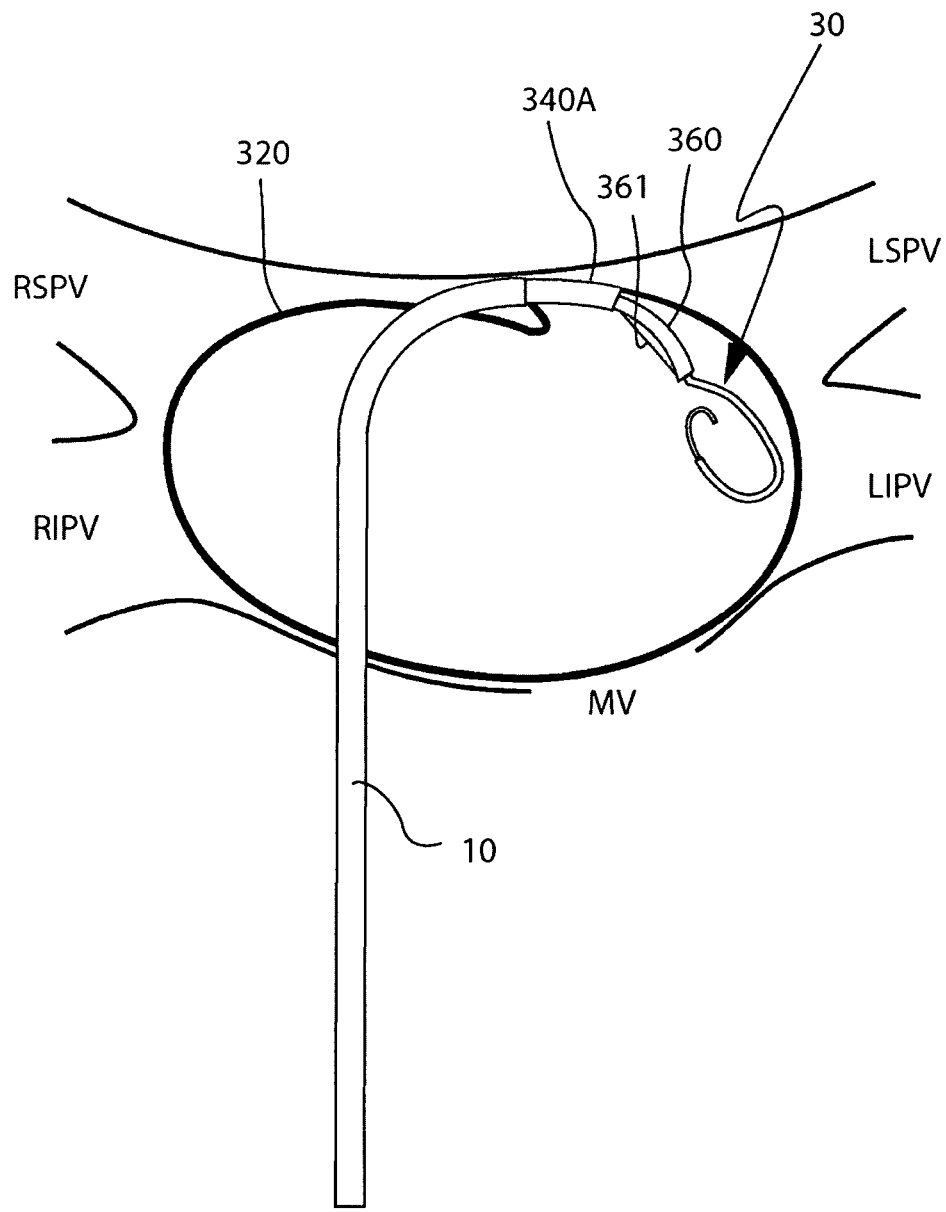
Figure 13C:
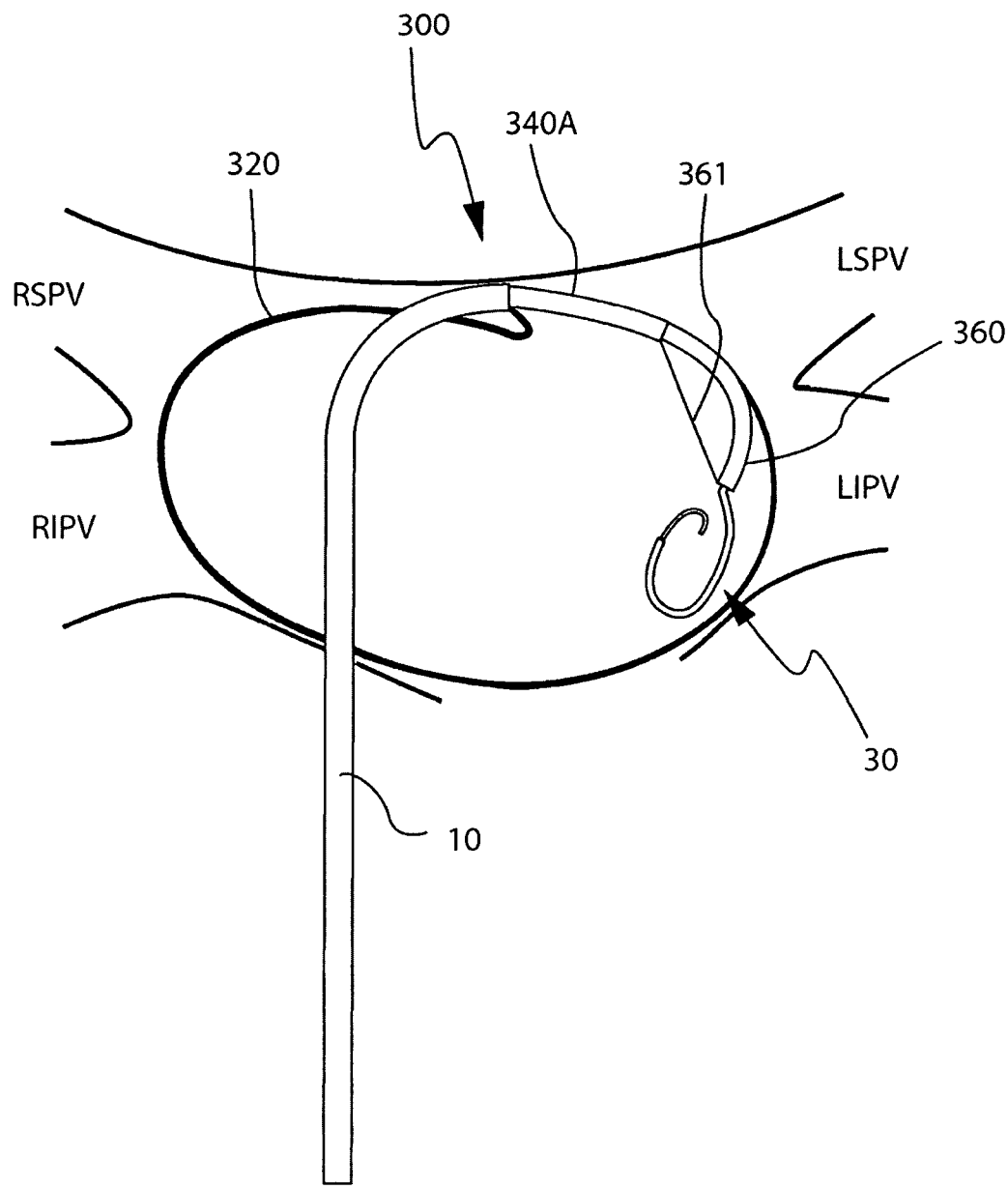

FIG. 13, and specifically FIGS. 13B and 13C further depict an alternative positioning element 340A which is formed from a coil of wire, such as a spring of suitable flexibility, as described herein with respect to positioning element 340. The positioning element 340A is integrated to the rail 320 through a fixed attachment point along the length of element 340A and rail 320. Such attachment may be achieved through any suitable means such as soldering or welding. Springy member 340A provides the functionality as described herein with respect to positioning element 340.

Figure 14:
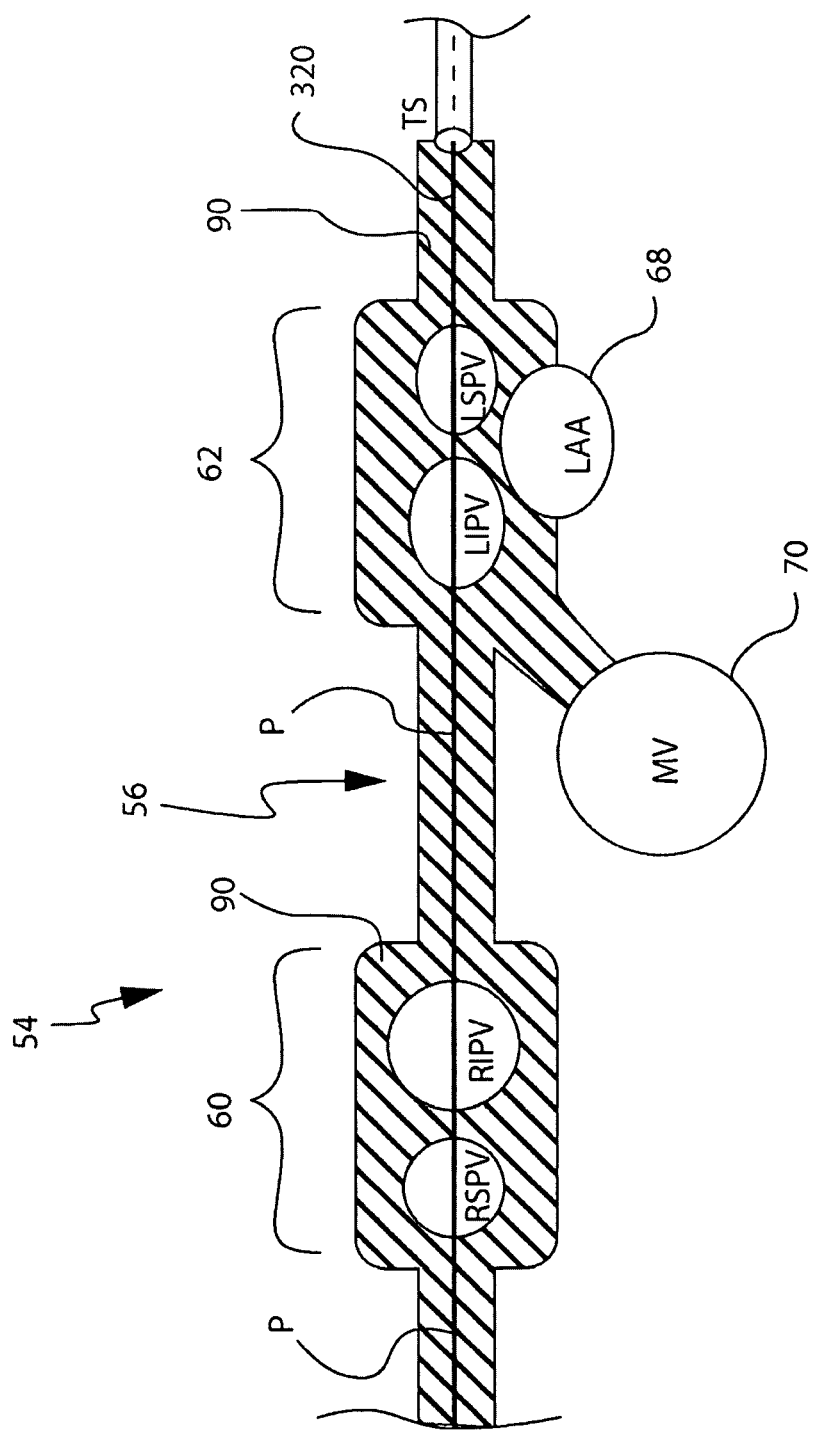
FIG. 14 is a planar depiction of an exemplary lesion pattern within the left atrium of a patient's heart.
Figure 15A:
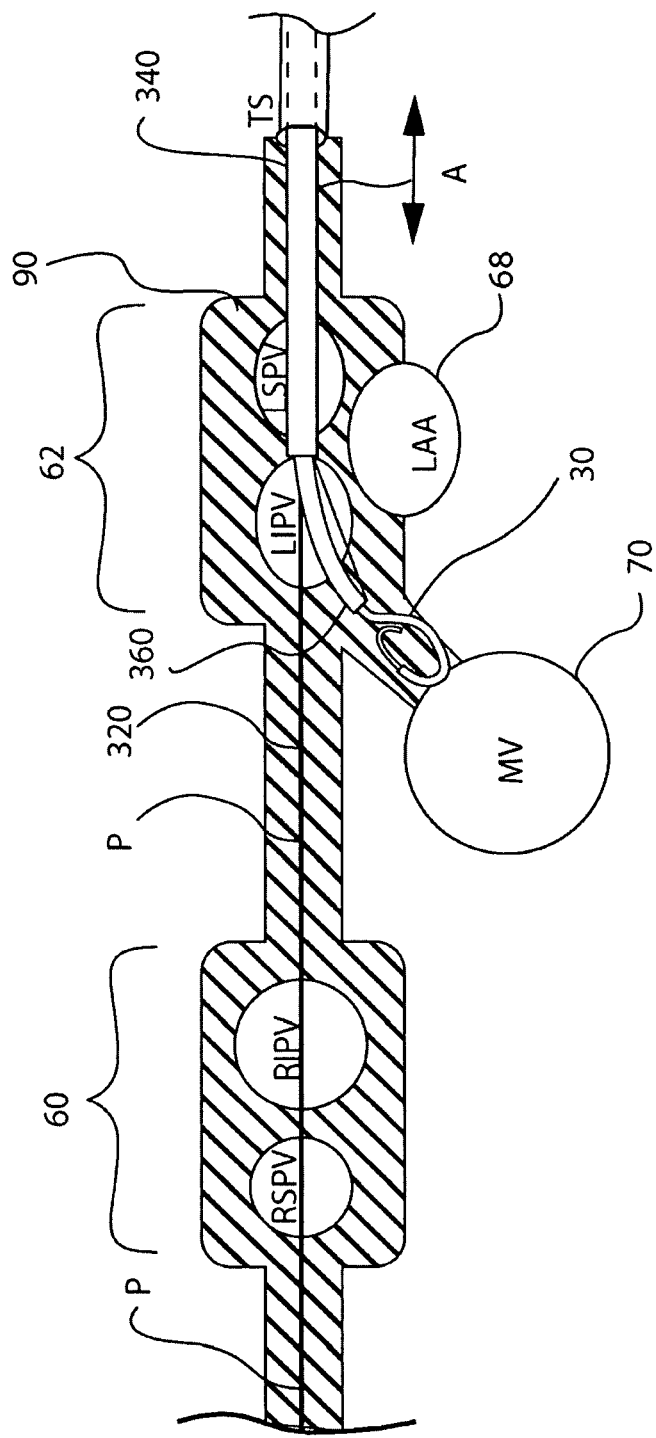
FIGS. 15A-15F are a series of planar views depicting the creation of a plurality of ablations with the delivery system of FIG. 8 and the ablation device of FIG. 10.
Figure 15B:
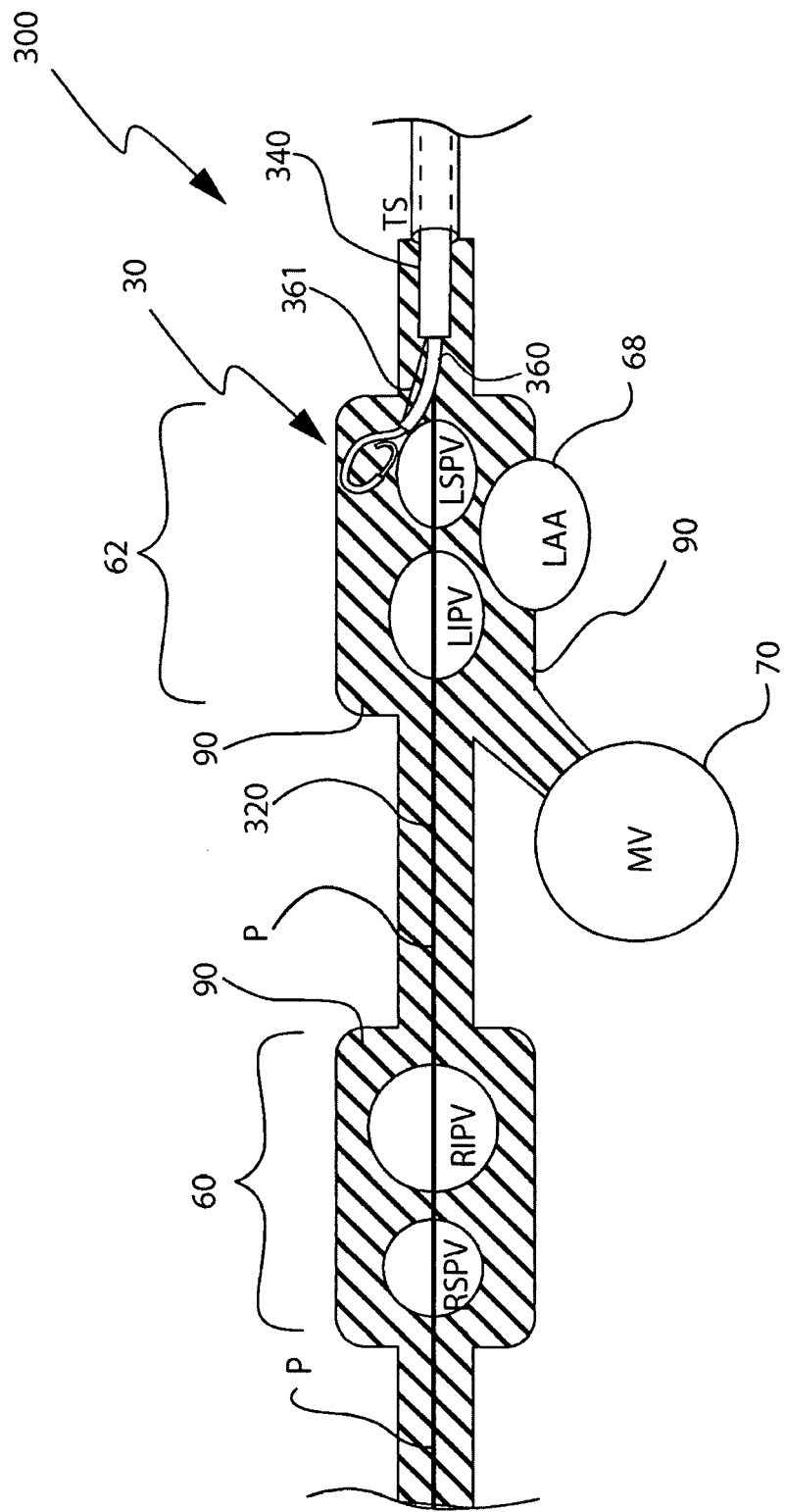
Figure 15C:
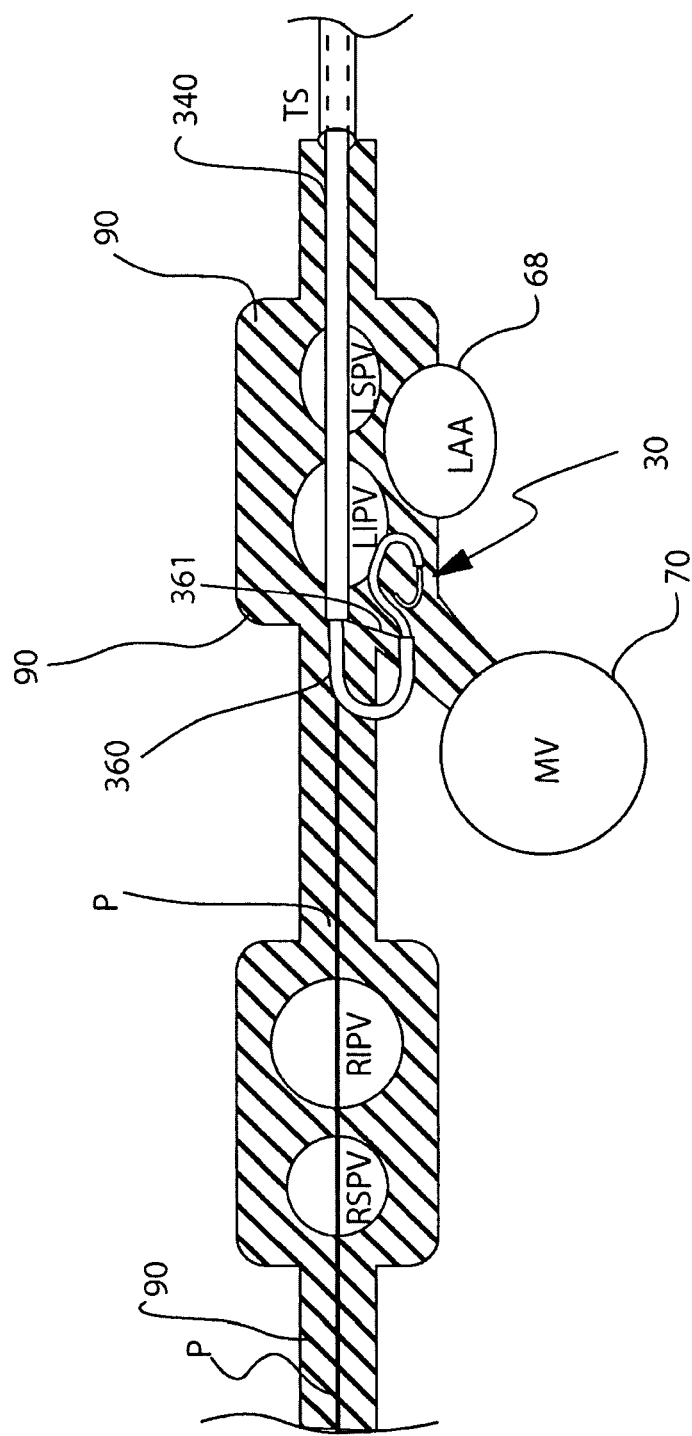
Figure 15D:
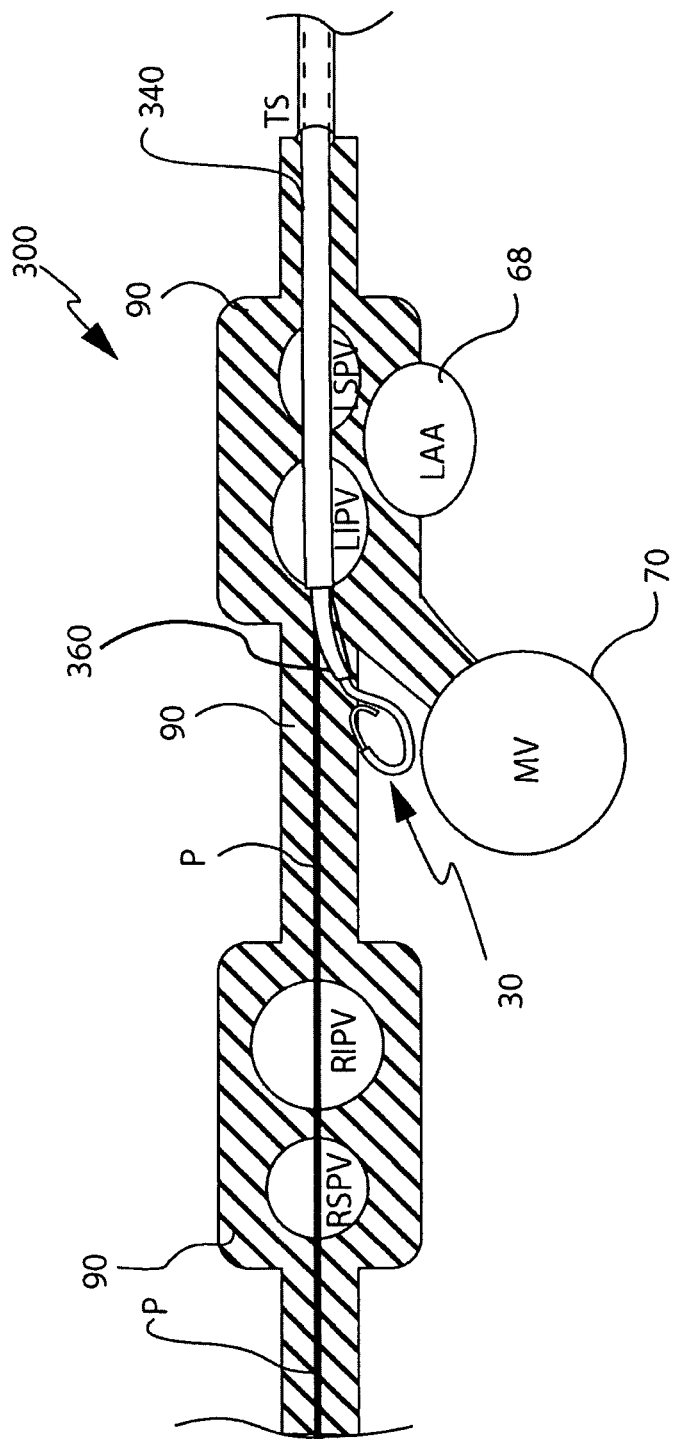
Figure 15E:
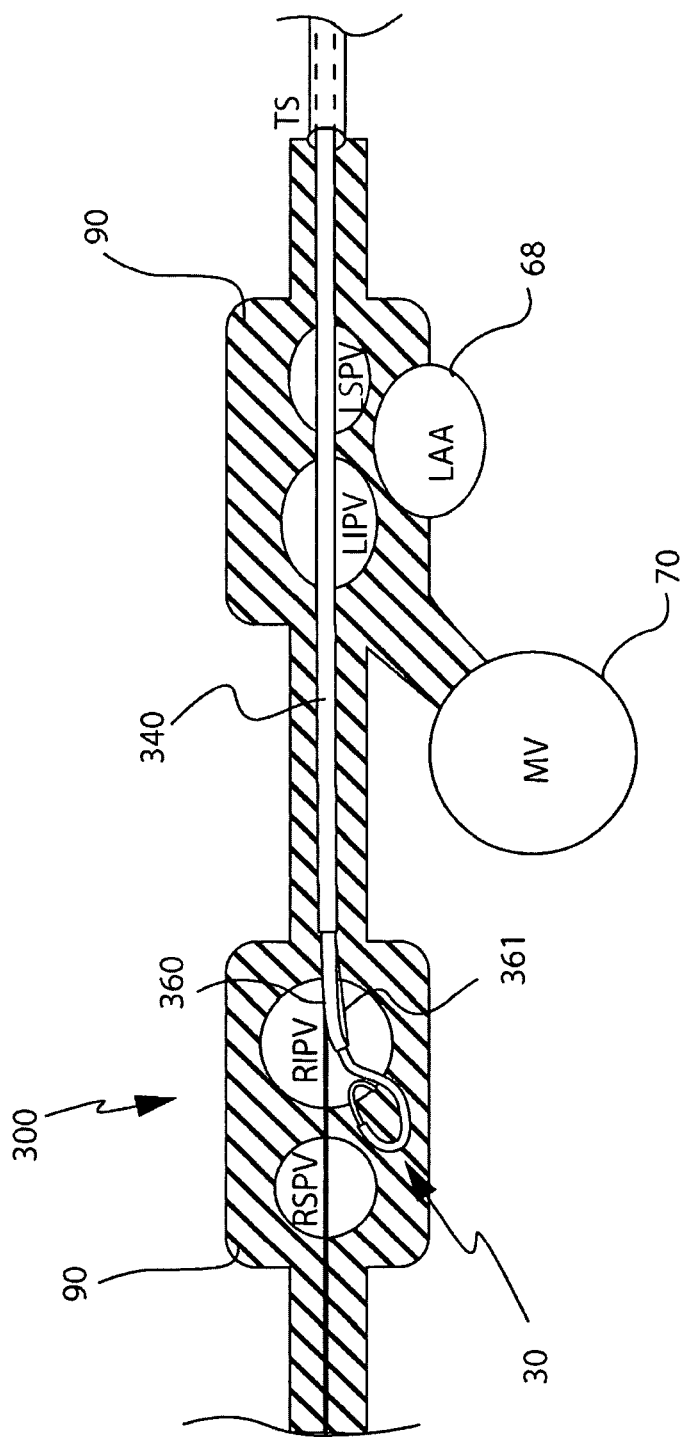
Figure 15F:
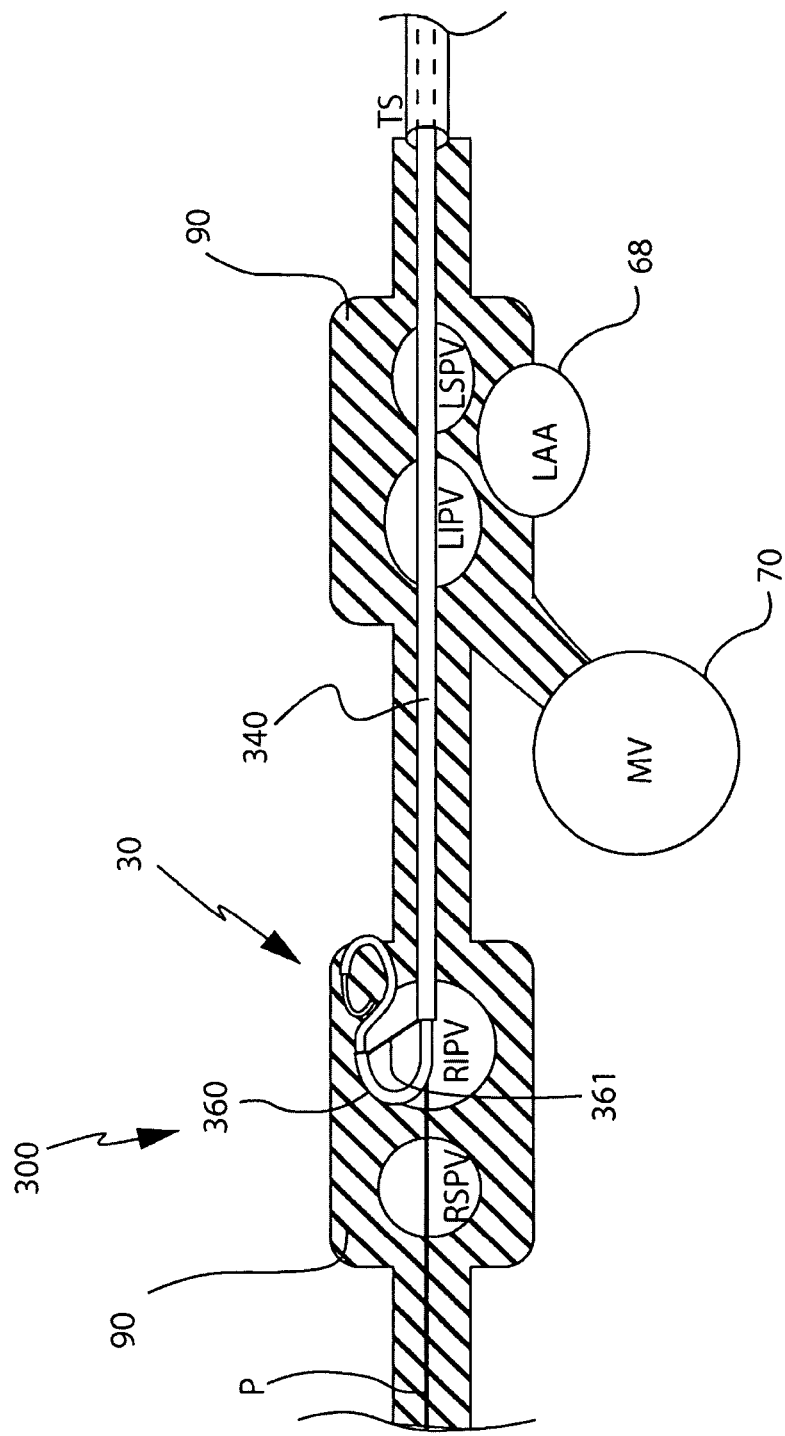

Now turning to FIG. 14, an exemplary lesion pattern 90, shown in shaded view, created through the use of delivery system 300 and ablation device 30 is discussed. FIG. 14 depicts the left atrium 54 of a patient's heart in a planar view for simplicity. The view is achieved through cutting along the medial line of the left atrium near the roof of the atrium and opening, or otherwise unfolding, the left atrium to depict the right superior and inferior pulmonary veins 60, RSPV and RIPV, respectively, and the left superior and inferior pulmonary veins 62, RSPV and RIPV, respectively. In such a configuration, the central area 56 refers to the area of atrial tissue between the mitral valve and the posterior wall of the heart, perhaps including a portion of the posterior wall. Also depicted is the mitral valve 70 (MV) and the left atrial appendage 68 (LAA). As discussed herein, the rail 320 of delivery system 300 is deployed generally in the pulmonary groove, as depicted in FIG. 14. Deployment of the guide rail 320 defines an operative path P. Further deployment of the positioning element 340, as discussed herein, will act to define a position along the path from which a functional device will be deployed. Additionally, a delivery sheath, such as sheath 360 described herein, can be used, the distal opening of the delivery sheath 360 further defining a position relative to the defined operative path P from which the functional device, ablation device 30 for example, is deployed.

FIGS. 15A-15F depict the various exemplary positioning of the ablation device 30 relative the operative path P for the creation of the desired lesion pattern 90. For simplicity, the positioning element 340, delivery sheath 360 and the ablating device 30 are depicted in shaded view, the numerical identifiers indicating approximate placement of the corresponding individual elements. From the discussion above, it should be apparent that the positioning element 340 delivery sheath 360 and the ablating device 30 cooperate together to define the final position of device 30 at a target tissue location. If required, delivery system 300 and/or ablating device 30 can include additional elements to assist the ablating procedure, such as electrodes 50 mounted upon the ablating device 30 or electrodes 370 mounted upon the delivery sheath 360, as discussed in greater detail above.

Tissue contact between the ablating device 30 and the target tissue is encouraged through application of a torsional force upon the delivery sheath 360. This is achieved, in part, through development of an offset distance between the ablating device 30 and the guide rail 320. As discussed above, one way to achieve this offset is through the application of a tension force to a pull wire 361 as a steering mechanism of delivery sheath 360 acting to deflect the distal portion 366 of delivery sheath 360.

Other advantages of the present invention become apparent when viewing FIGS. 15A-15F. For example, with specific reference to FIG. 15D, once an ablation, as part of pattern 90, is achieved at the depicted location of ablation device 30, additional ablations created along the atrial tissue between the LIPV and RIPV are achieved through simple translational movements of the positioning element 340 along the operative path P. That is, through the coordinated application of opposing tensile forces upon the proximal control sections 322, 342 of the guide rail 320 and positioning element 340 act to move the distal opening of the positioning element 340 along the defined operative path P. Therefore, as the proximal control section of the positioning element 340 is advanced and the proximal control section of the guide rail 320 is correspondingly retracted, smooth, accurate and reliable movement of the distal end of positioning element 340 is achieved. Depending on the surface texture of the left atrial tissue, it may be more suitable to first completely deploy the distal end of positioning element 340 to the end of the operative path and then retract the positioning element 340, and the ablating device 30, along the path. In this way, the ablating device 30 can more freely move across the atrial tissue surface.

Another advantage of the present invention is that mirroring ablations, that is ablations on opposing tissue surfaces of the operative path, such as those tissue surrounding the left and right pulmonary veins, can be more accurately and reliably created. With specific reference to FIGS. 15B-15F, in each depicted position of ablating device 30, an ablation which mirrors the depicted ablation, with respect to the operative path, can be easily created. The delivery sheath 360 is simply rotated with respect to the positioning element 340 such that the ablating device 30 engages the tissue at the mirrored location. Further application of torsion upon the delivery sheath 360 can be made to encourage the desired contact between the ablating device 30 and the target tissue. Application of ablative energy is then applied and the mirrored ablation is then created.

Still another advantage of the present invention is that the various ablations, as part of the desired lesion pattern 90, can be easily created through repositioning the ablating device 30 to a previous position, if desired. This is achieved through controlled movement of the ablating device through cooperative operation of the proximal control sections 322, 324 of the positioning element 340 and guide rail 320. That is, as described in greater detail above, such a control can be a linear control on a handle portion (not shown) which divides the operative path into one or more positions, each position relative to the dimensions of the functional device, less than the length of the ablating device 30 for example. In this way a series of ablations can be created, one at least at each position, the combination of all created ablations providing the continuous lesion pattern, pattern 90 for example. With the operative path defined into one or more positions, the user can easily move from one position to any other position, as part of the define operative path, through simple user inputs, allowing for the performance of additional medical procedures, or reapplication of medical procedures, such as ablation procedures, at those positions.

A further advantage of the present invention is depicted in FIGS. 15A-15F. More specifically, the present invention allows for the simple creation of various lesions, as part of a desired lesion pattern 90, through simply user inputs without requiring the need to constantly reposition the delivery system 300. Since the delivery system 300 is adapted to provide a stable platform from which a junctional device, such as ablation device 30, is deployed once the delivery system is deployed defining a desired operative path, all that remains is the advancement of the ablating device 30 with respect to that path. Such translation, as described herein, is achieved through simple coordinated movements performed by the present invention and not relying on special skills of the user.

This is very advantageous with respect to prior art ablating devices where the ablating portion is limited to the deployed loop structure of the device itself. Such prior art ablation systems require constant redeployment for the completion of a desired lesion set, without the ability to accurately and reliably return to a previous location for additional ablations, or performance of additional medical procedures as desired, at those locations.

Given these advantages, various medical procedures, such as ablation procedures related to cardiac arrhythmias, can be more easily performed through accurate and reliable placement of one or more functional devices at various positions relative a defined operative path. Such procedures can be performed more effectively requiring less time which reduces procedural costs. Procedural costs can be further reduced since costly imaging systems are generally not required to track the position or progress of the procedure.

While the above discussion has been in terms of delivery system 300, it should be apparent that the advantages discussed with respect to delivery system 300 equally apply to other deliver system, and/or ablation system, embodiments described or disclosed herein.

The present invention described and disclosed herein is applicable to the delivery of various medical devices within a body for performance of one or more medical procedures. The present invention provides a position relative to a defined operative path from which a medical device can be deployed, accurately and reliably, for the performance of one or more associated medical procedures. The present invention should not be considered limited to the particular examples described above. Various modifications, equivalent processes, as well as numerous structures to which the present invention may be applicable will be readily apparent to those of skill in the art to which the present invention is directed, upon review of the present specification.

We claim:

1. A medical device comprising:
a sheath having a near portion, a deflectable far portion, and at least a first lumen extending therethrough;
a functional device deployable from the first lumen, the functional device comprising a transmission line capable of transmitting electromagnetic energy and having planar loop section advanceable out of the far portion of the sheath;
the planar loop section comprising one or more electrodes along a length of the planar loop section and a distal end comprising a radiating portion having a length selected such that the radiating portion cooperates with a remainder of the planar loop section to distribute electromagnetic energy about the planar loop section and confined to an outer boundary of the planar loop section.

2. The medical device of claim 1, where the deflectable far portion further comprises at least one pull wire coupled thereto.

3. The medical device of claim 1, further comprising a first steering arm moveable on the first portion of the member, where a proximal end of the first steering arm allows manipulation of the a distal end of the first steering arm to alter the shape of loop section;
a second steering arm moveable on the second portion of the member, where a proximal end of the second steering arm allows manipulation of a distal end of the second steering arm to alter the shape of loop section; and
wherein the member is configured such that axial movement of the first and/or second portion of the member through the sheath alters a size of the loop section, and manipulation of the first and/or second steering arms alters the shape of the loop section.

4. The medical device of claim 1, where the transmission line includes a center conductor surrounded by a layer of dielectric material surrounded by an outer conductor.

5. The medical device of claim 4, where the radiating portion is formed by removing the outer conductor from a distal portion of the transmission line.

6. The medical device of claim 1, where the radiating portion comprises a central conductor and surrounding dielectric material.

7. The medical device of claim 1, where the deflectable far portion of the sheath has a flexibility greater than that of the remaining portion of sheath.

8. The medical device of claim 1, where the deflectable far portion of the sheath is preshaped.

9. A method of guiding a medical device along a path in an anatomy of a patient, the method comprising:
navigating a sheath towards the anatomy, where the sheath includes a near portion, a far portion, and at least a first lumen extending therethrough, the sheath including a member located within the lumen, the member having a first and second portions extending from a near portion of the sheath, and a loop section located therebetween, where the loop section is advanceable out of the far portion of the sheath;
defining a path in the anatomy by advancing at least one portion of a rail to adjust a size of the loop section in the anatomy;
altering the profile of the path by manipulating at least one steering arm coupled to a portion of the member, where manipulation of the steering arm alters the loop section to alter the path in the anatomy;

advancing the medical device along the loop section to position the medical device along the path in the anatomy.

10. The method of claim 9, further comprising altering the profile of path by manipulating at least a second steering arm coupled to a second portion of the member.

11. The method of claim 9, where defining the path in the anatomy comprises creating an access path to multiple regions in an atrium of a heart.

12. The method of claim 11, where defining the path in the anatomy comprises defining the path to structures selected from the group consisting of to the Left Superior Pulmonary Vein, Left Inferior Pulmonary Vein, Right Superior Pulmonary Vein, Right Inferior Pulmonary Vein, and the Mitral Valve Annulus.

\* \* \* \* \*